(12) United States Patent
Anderson et al.

(10) Patent No.: US 6,733,747 B2
(45) Date of Patent: May 11, 2004

(54) PROSTHETIC GRAFTS

(75) Inventors: Diane Lee Anderson, Dripping Springs, TX (US); John Paul Ranieri, Austin, TX (US); Maurizio Capogrossi Colognesi, Rome (IT); Marco Scoccianti, Rome (IT); Antonio Facchiano, Rome (IT)

(73) Assignee: Centerpulse Biologics Inc., Houston, TX (US)

(*) Notice: Subject to any disclaimer, the term of this patent is extended or adjusted under 35 U.S.C. 154(b) by 0 days.

(21) Appl. No.: 09/978,986

(22) Filed: Oct. 15, 2001

(65) Prior Publication Data

US 2002/0026235 A1 Feb. 28, 2002

Related U.S. Application Data

(62) Division of application No. 09/300,351, filed on Apr. 27, 1999, now Pat. No. 6,328,762.

(51) Int. Cl.[7] .................. A61K 48/00; A01N 63/00; C12D 21/06; C12N 5/02; A61F 2/06
(52) U.S. Cl. .................. 424/93.21; 424/93.1; 424/93.2; 435/69.1; 435/325; 435/455; 623/1.41; 623/1.39; 623/1.1
(58) Field of Search ................ 623/1.1–3.3; 424/93.21, 424/93.2, 93.1; 435/69.1, 325, 455

(56) References Cited

U.S. PATENT DOCUMENTS

| | | |
|---|---|---|
| 4,539,716 A | 9/1985 | Bell ........................... 623/1 |
| 4,648,881 A | 3/1987 | Carpentier et al. ........... 623/11 |
| 4,804,381 A | 2/1989 | Turina et al. ................. 623/1 |
| 4,868,116 A | 9/1989 | Morgan et al. ........... 435/240.2 |
| 5,219,739 A | 6/1993 | Tischer et al. ............. 435/69.4 |
| 5,219,740 A | 6/1993 | Miller et al. ............... 435/69.6 |
| 5,230,693 A | 7/1993 | Williams et al. ............. 600/36 |
| 5,370,681 A | * 12/1994 | Herweck et al. ........... 623/1.27 |
| 5,399,346 A | 3/1995 | Anderson et al. ........ 424/93.21 |
| 5,443,950 A | 8/1995 | Naughton et al. ............. 435/1 |
| 5,455,039 A | 10/1995 | Edelman et al. ............. 424/422 |
| 5,460,959 A | 10/1995 | Mulligan et al. .......... 435/172.3 |
| 5,492,826 A | 2/1996 | Townsend et al. ....... 435/240.23 |
| 5,527,532 A | 6/1996 | Edelman et al. ............. 424/422 |
| 5,540,928 A | 7/1996 | Edelman et al. ............. 424/422 |
| 5,575,815 A | 11/1996 | Slepian et al. ................ 623/1 |
| 5,674,722 A | 10/1997 | Mulligan et al. .......... 435/172.3 |
| 5,705,732 A | 1/1998 | Sims et al. .................... 800/2 |
| 5,723,324 A | 3/1998 | Bowlin et al. ............ 435/173.6 |
| 5,762,926 A | 6/1998 | Gage et al. ............... 424/93.21 |
| 5,766,584 A | 6/1998 | Edelman et al. ........... 424/93.7 |
| 5,785,965 A | 7/1998 | Pratt et al. ............... 424/93.21 |
| 5,800,512 A | 9/1998 | Lentz et al. ................. 623/12 |
| 5,811,151 A | 9/1998 | Hendriks et al. .......... 427/2.24 |
| 6,328,762 B1 | * 12/2001 | Anderson et al. .......... 623/1.41 |
| 6,443,941 B1 | * 9/2002 | Slepian et al. .............. 604/522 |

OTHER PUBLICATIONS

Game et al, Wien Klin Wochenschr 2001;113:82–38.*
Lafont et al, Ann. Card. Ang. 44(7): 49–59/1995.*
Johnson et al, Thromb Haemost 1999;81:835–43.*
Donovan and Gearhart, Nat 2001 Nov.;414:92–97.*
Weissman, Science 2000;287:1442–46.*
Robbins et al, Pharmacol Ther 1998;80:35–47.*
Verma et al, Nature 1997;389:239–42.*
Boucher et al, J Clin Invest 1999 Feb.; 103:441–5.*
Andrew et al, Curr Opin Cardiol 1999;14:489–494.*

* cited by examiner

Primary Examiner—Deborah J. Reynolds
Assistant Examiner—Q. Janice Li
(74) Attorney, Agent, or Firm—Sheridan Ross

(57) ABSTRACT

An improved prosthetic graft for the bypass, replacement or repair of vessels and organs that are in contact with blood flow is disclosed. The prosthetic graft includes a porous prosthetic implant and adherent cells adhered to the outer surface of the implant. The adherent cells are transfected with at least one recombinant nucleic acid molecule encoding at least one protein that enhances patency of the graft. The prosthetic graft has a long-term patency and success rate that is superior to other previously described prosthetic grafts designed for such use. Also disclosed are methods of making and using such a graft.

18 Claims, 13 Drawing Sheets

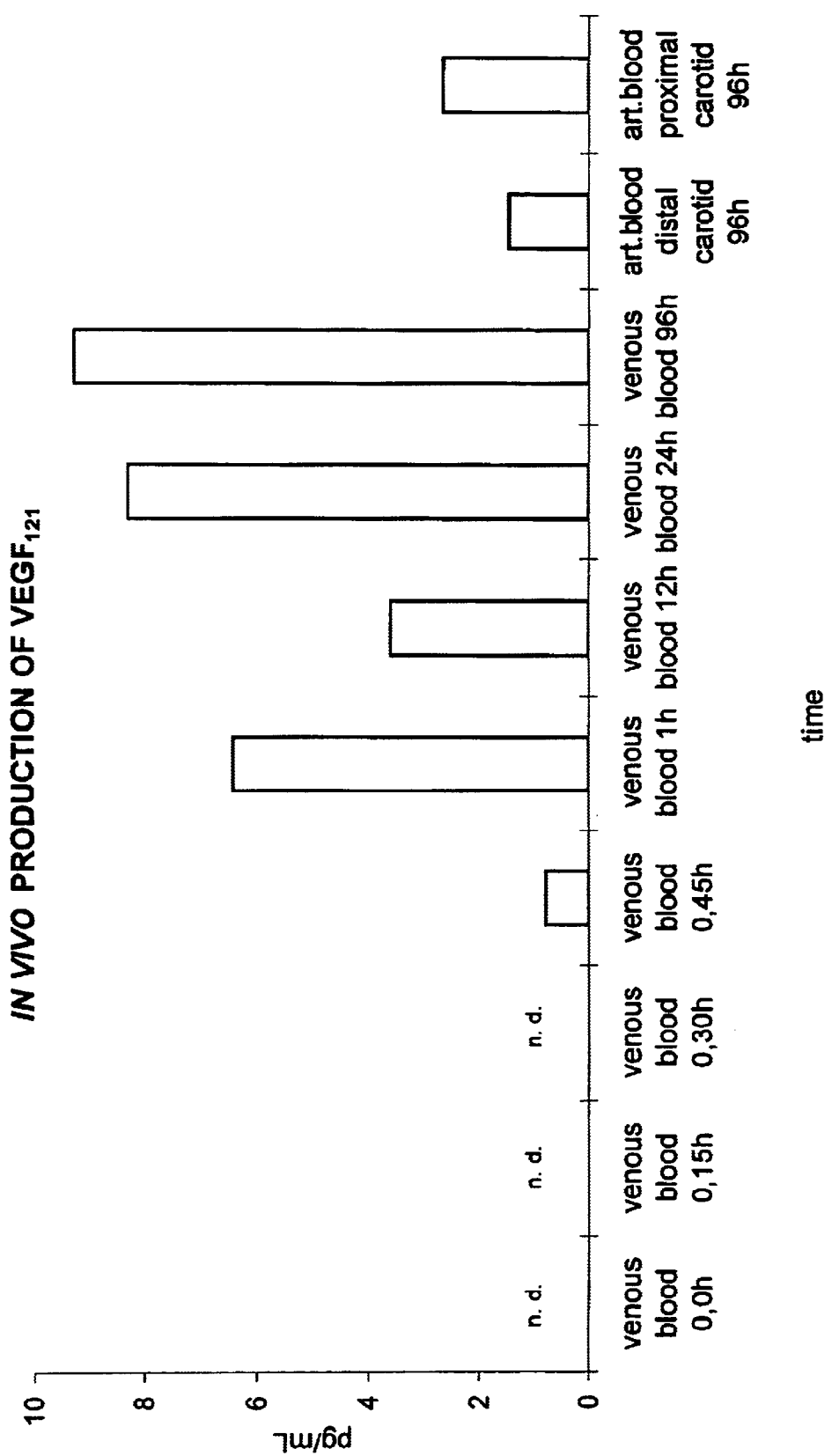

PROSTHETIC GRAFTS

This application is a divisional of U.S. patent application Ser. No. 09/300,351, now U.S. Pat. No. 6,328,762 B1 filed Apr. 27, 1999. The entire disclosure of U.S. patent application Ser. No. 09/300,351 is incorporated herein by reference.

FIELD OF THE INVENTION

The present invention relates to prosthetic grafts which are used to contain blood flow in vivo.

BACKGROUND OF THE INVENTION

Diseases of the major circulatory and renal organs and vessels have created a need for prosthetic grafts to bypass, repair and/or replace the function of the diseased organs and vessels. Such grafts should ideally be non-immunogenic, non-calcific, and readily capable of recreating or reestablishing the natural blood contact interface of the organ or vessel to be replaced or repaired. Complications that have inhibited the widespread use of prosthetic grafts in organs and vessels in contact with blood include: (1) intimal hyperplasia, whereby smooth muscle cell and myofibroblast proliferation and extracellular matrix accumulation cause thickening of the intima in the graft and in the adjoining vessels, and ultimately lead to failure of the graft; and, (2) occlusion of the graft, whereby platelet adhesion and activation at the lumenal surface of the graft initiates thrombosis which, particularly in smaller bore vessel grafts, typically leads to complete occlusion of the graft.

Research over the past several decades has yet to produce a synthetic or biosynthetic small bore vascular graft which can approach the patency rates of autologous vessels. Since small bore grafts have a higher surface area to volume ratio and lower flow rates than larger grafts, the interaction of the graft with the blood is much greater. Platelet adhesion and activation at the lumenal surface of the graft are much more likely to result in complete graft occlusion. Larger vascular grafts are able to remain patent despite a layer of clot lining the lumen because this layer of clot undergoes constant remodeling and essentially maintains a constant thickness. In contrast, clotting on the surface of a graft smaller than 6 mm in inner diameter has a snowball effect and results in a continuous growth of the surface clot until the entire graft is occluded.

Currently, non-synthetic or biological small bore grafts are routinely used as an arterial replacement since nothing has proven to perform nearly as well as the autologous saphenous vein or internal mammary artery, which are the conventional biological materials used as a small diameter vascular graft. The use of these vessels requires additional surgery, particularly in the case of the saphenous vein, whereby the entire length of the leg must be opened to remove the vessel. The harvesting surgery increases the total operating time and can also lead to complications and discomfort. Furthermore, a small percentage of patients do not have autologous vessels suitable for harvesting. In some cases, the vessels are not available due to previous surgery, while in other cases, the vessel may be too small or varicose.

Even larger bore vessel and organ prosthetic grafts, however, suffer from complications associated with smooth muscle proliferation, compliance mismatch with native vessels, and poor endothelialization due to blood shear stresses and mechanical damage. Therefore, researchers have focused much effort on the development of bioinert and hemocompatible graft materials. However, a completely non-fouling surface has yet to be discovered and many now view the quest for such a material as unrealistic.

Rather than creating a non-fouling surface, others have focused on recreating the natural blood contacting interface in the body by seeding vascular grafts with endothelial cells (See for example, U.S. Pat. No. 5,723,324 to Bowlin et al.; U.S. Pat. No. 5,674,722 to Mulligan et al., U.S. Pat. No. 5,785,965 to Pratt et al., U.S. Pat. No. 5,766,584 to Edelman et al.). Although a small number of grafts seeded lumenally with endothelial cells have been implanted clinically outside of the United States, and improved patencies over non-seeded grafts have been observed, this approach has generally enjoyed mixed success, and the concept still faces many challenges. First, it is necessary that the cells used to seed the graft be autologous or otherwise non-immunogenic to avoid recognition and destruction of the cells by the patient's immune system. To obtain autologous endothelial cells from a patient, the cells must be harvested from an isolated blood vessel. The harvesting surgical procedure not only increases prosthetic implant preparation time, but can also lead to complications and discomfort for the patient.

Second, retention of the cells on the graft surface after implantation has been an issue. A number of methods have been disclosed to address this issue, and include forcible injection of endothelial cells into the graft, preclotting and seeding the lumenal surface of the graft, static adhesion-seeding of the lumen, vacuum seeding of the lumen, seeding the lumen in an extracellular matrix, and seeding of the lumen using electrostatic and gravitational forces. These methods are reviewed or disclosed in more detail in U.S. Pat. No. 5,723,324, ibid. Additionally, it has been suggested that flow conditioning the seeded graft in vitro prior to implantation would improve cell retention by allowing the cells to secrete adhesion factors in response to slowly increasing shear rates (Dardik et al., 1999, *J Vasc Surg* 29: 157–67; Ballerman et al., 1995, *Blood Purif* 13: 125–34; and Ott and Ballerman, 1995, *Surgery* 117: 334–9). Although there is some evidence that methods such as conditioning may improve cell retention, all of these methods add yet another level of complexity to the seeding process and it is still not clear that significantly improved cellular retention can be achieved.

Therefore, there is a need for prosthetic grafts for use in the repair and replacement of vessels and organs in contact with blood flow that have improved long term patency and success rates, and which reduce the stress and discomfort experienced by the patient.

SUMMARY OF THE INVENTION

One embodiment of the present invention relates to a prosthetic graft for containment of blood flow in vivo. The graft includes: (a) a porous prosthetic implant for containing blood in vivo, the prosthetic implant having an outer surface that is not in contact with blood flow in vivo and an inner surface that is in contact with blood flow in vivo, the inner surface defining an interior space for containment of blood flow; and, (b) adherent cells adhered to the outer surface of the porous prosthetic implant. The adherent cells are transfected with at least one recombinant nucleic acid molecule operatively linked to a transcription control sequence, the recombinant nucleic acid molecule encoding a protein that enhances patency of said prosthetic implant.

The prosthetic implant can be configured as any blood containing vessel including, but not limited to, a prosthetic vessel, an artificial heart, a left ventricle assist device and/or a dialysis shunt. Prosthetic vessels include small, medium and large bore prosthetic vessels. Such vessels include venous and arterial prosthetic vessels. The implant can be constructed of any biological or non-biological material which includes, but is not limited to, highly resilient polyester, expanded polytetrafluorethylene (ePTFE), high porosity ePTFE, non-immunogenic xenogeneic tissue, porous silicon rubber, porous polyurethane, porous degradable polymer, and/or porous copolymers. In preferred embodiments, the prosthetic implant is non-immunogenic, non-calcific, and/or has a pore size of from about 0.1 $\mu$m to about 500 $\mu$m, and more preferably, from about 0.2 $\mu$m to about 100 $\mu$m.

The adherent cells can be any adherent cells and include, but are not limited to, fibroblasts, mesenchymal stem cells, bone marrow stem cells, embryonal stem cells, adipocytes, keratinocytes, vascular smooth muscle cells, platelets, and cells which have been genetically engineered to be adherent. In one embodiment, the cells are fibroblasts. The cells are transfected with at least one recombinant nucleic acid molecule encoding at least one protein that enhances patency of the prosthetic implant. Such proteins can include, but are not limited to, a protein that enhances angiogenesis in the vascular bed downstream of the prosthetic graft, a protein that enhances angiogenesis transmurally and into the interior space of the prosthetic implant to endothelialize the inner surface of the prosthetic implant, a protein that inhibits thrombosis, a protein that causes thrombolysis, a protein that inhibits smooth muscle migration and/or proliferation, and a vasodilator protein. Specific examples of such proteins are described in detail below.

In one embodiment of the present invention, the proteins are expressed by the adherent cells ex vivo, and secreted by the cells ex vivo and/or in vivo. In another embodiment, the proteins are expressed and secreted by the adherent cells in vivo. Preferably, the proteins are secreted into the pores of the implant and perfuse through the pores and into the inner surface of the implant. In one embodiment, the transcription control sequence includes an inducible promoter, so that the expression of the protein can be up- and/or down-regulated ex vivo or in vivo. Such an inducible promoter can be regulated, for example, by a compound that induces the promoter, including, but not limited to, an antibiotic, a hormone, a transcription factor and/or by a treatment such as internal or external radiation (e.g., X-ray).

Another embodiment of the present invention relates to a vascular graft, which includes: (a) a porous prosthetic vessel having a perivascular surface and a lumenal surface; and (b) adherent cells adhered to the perivascular surface of the porous prosthetic vessel. The adherent cells are transfected with at least one recombinant nucleic acid molecule operatively linked to a transcription control sequence, the recombinant nucleic acid molecule encoding a protein that enhances patency of the prosthetic vessel.

Yet another embodiment of the invention relates to a prosthetic graft for containment of blood flow in vivo which includes: (a) a porous prosthetic implant for containing blood in vivo, having an outer surface that is not in contact with blood flow in vivo and an inner surface that is in contact with blood flow in vivo, whereby the inner surface defines an interior space for containment of blood flow; and, (b) adherent cells adhered to the outer surface of the porous prosthetic implant. In this embodiment, the adherent cells express and secrete a protein that enhances patency of the prosthetic implant. In one aspect of this embodiment of the present invention, the adherent cells are endothelial cells that have been genetically modified to be adherent.

Yet another embodiment of the present invention relates to a method for producing a prosthetic graft, which includes the step of applying adherent cells to a porous prosthetic implant for containing blood in vivo, wherein the prosthetic implant has an outer surface and an inner surface that defines an interior space for containment of blood flow. The adherent cells are applied to the outer surface of the prosthetic implant. The adherent cells are transformed with at least one recombinant nucleic acid molecule operatively linked to a transcription control sequence, the recombinant nucleic acid molecule encoding a protein that enhances patency of the prosthetic implant. Other characteristics of the prosthetic implant are described above. Such a method preferably enhances naturally occurring endothelialization of the inner surface of the implant, inhibits thrombosis in the implant, inhibits thrombosis of the inner surface of the prosthetic implant due to smooth muscle migration and/or proliferation in the implant, and/or enhances formation of a neointima in the inner surface of the implant.

The step of applying can be performed by any method, including by a programmable mechanical graft rotator. When the implant is a prosthetic vessel, the step of applying includes seeding the outer surface of the vessel uniformly in both radial and longitudinal directions on the vessel. In one embodiment, the graft is incubated after the step of applying for about 5 minutes to about 14 days.

Another embodiment of the present invention relates to a method of implantation of a prosthetic graft for containment of blood flow. Such a method includes the step of implanting a prosthetic graft as described above into a patient. In one embodiment, the adherent cells are autologous to the patient. In another embodiment, the adherent cells are from a cell selected from the group of undifferentiated stem cell lines and/or embryonal cell lines.

If the transcription control sequence operatively linked to the at least one recombinant nucleic acid molecule includes an inducible promoter, the cells can be induced to express the protein either in vitro, prior to implantation of the graft into a patient, or in vivo, after implantation of the graft into a patient. Other characteristics of such a graft are described above.

Yet another embodiment of the present invention relates to a method for implantation of a prosthetic graft for containing blood flow in a patient. Such a method includes the steps of: (a) harvesting fibroblast cells from a patient in need of a prosthetic graft for containing blood flow; (b) transfecting the fibroblast cells with an isolated nucleic acid molecule encoding a protein that enhances patency of the graft; (c) applying the transfected fibroblast cells onto a surface of a prosthetic implant configured for containing blood flow in vivo for a time sufficient to allow the fibroblast cells to adhere to the surface to form a prosthetic graft, wherein the surface is not in contact with blood flow in vivo; and, (d) implanting the prosthetic graft into the patient.

Another embodiment of the present invention relates to a method of enhancing endothelialization of a vascular graft. Such a method includes the step of applying adherent cells to a porous prosthetic vessel having a perivascular surface and a lumenal surface, wherein the adherent cells are adhered to the perivascular surface of the prosthetic vessel. The adherent cells are transfected with at least one recombinant nucleic acid molecule operatively linked to a transcription control sequence, the recombinant nucleic acid molecule encoding a protein that enhances endothelialization of the prosthetic vessel. The protein is expressed and secreted by the adherent cells and perfuses through pores in the prosthetic vessel to the lumenal surface of the prosthetic vessel to enhance endothelialization of the graft at the inner surface.

BRIEF DESCRIPTION OF THE FIGURES OF THE INVENTION

FIG. 4 is a bar graph showing production of VEGF in vivo by a prosthetic graft of the present invention.

DETAILED DESCRIPTION OF THE INVENTION

Figure 1A:
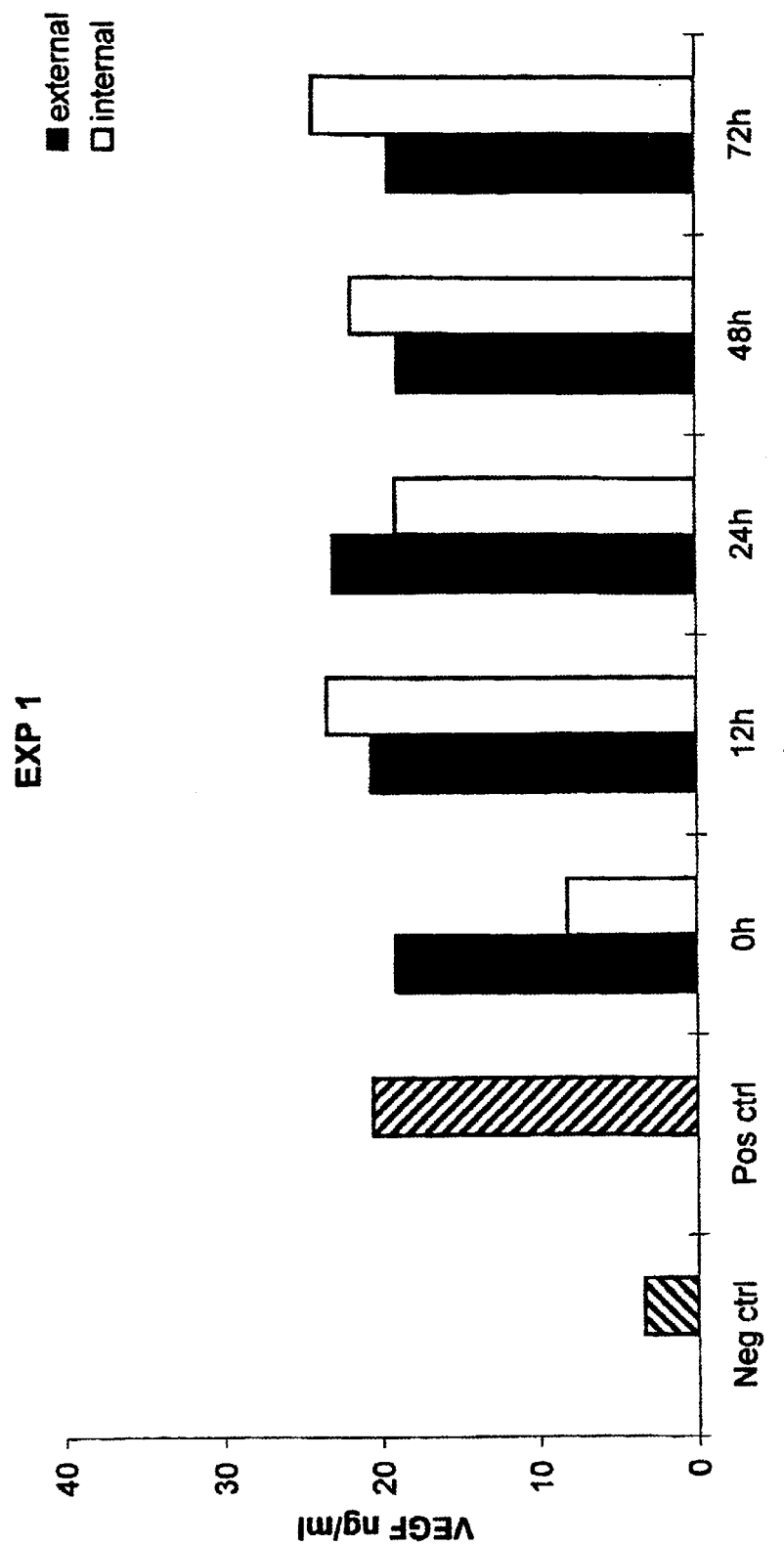
FIG. 1A is a bar graph showing the release of VEGF under static conditions by a prosthetic graft of the present invention.

The present invention generally relates to an improved prosthetic graft and methods of making and using such a graft, for the bypass, replacement or repair of vessels and organs that are in contact with blood flow. The prosthetic graft of the present invention has a long-term patency and success rate that is superior to other previously described prosthetic grafts designed for such use.

More particularly, one embodiment of the present invention relates to a prosthetic graft for containment of blood flow in vivo. The prosthetic graft comprises a porous prosthetic implant for containing blood in vivo, wherein the prosthetic implant has an outer surface that is not in contact with blood flow in vivo and an inner surface that is in contact with blood flow in vivo. The inner surface defines an interior space for containment of blood flow. The prosthetic graft additionally includes adherent cells that are adhered to the outer surface of the porous prosthetic implant. The adherent cells are transfected with at least one recombinant nucleic acid molecule operatively linked to a transcription control sequence, and each recombinant nucleic acid molecule encodes one or more proteins that enhance patency of the prosthetic implant.

The present inventors have discovered that prosthetic implants of the present invention have several advantages over other prosthetic grafts of the same type which are currently known in the art.

First, the use of adherent cells which recombinantly produce one or more proteins that enhance patency of the prosthetic implant eliminates the need to seed the lumenal surface of the graft with endothelial cells or with proteins to enhance the endothelialization and neovascularization of the graft. Prior to the present invention, considerable research effort has been expended to determine suitable means of seeding grafts with endothelial cells to enhance the natural neovascularization processes. Other groups have provided selected proteins directly to the graft lumenal or extralumenal surface for similar reasons. When proteins are directly provided to the graft, special care must be taken to ensure sterility of the proteins. Efforts to sterilize the proteins and deliver and maintain the proteins at the graft for a time sufficient to provide a therapeutic benefit introduces problems associated with degradation of the proteins and/or loss of protein activity.

In contrast, in the prosthetic graft of the present invention, the adherent recombinant cells express and secrete one or more proteins which diffuse through the porous prosthetic implant to the lumenal surface of the graft, whereby the proteins are effective to enhance patency, including inducing natural neovascularization and particularly, endothelialization, of the graft, as well as inhibiting processes which would cause occlusion and failure of the graft (i.e., thrombosis, smooth muscle cell migration and proliferation, platelet adhesion and activation, extracellular matrix accumulation). Cell culture and graft seeding can easily be accomplished under sterile conditions ex vivo, and the need to sterilize individual proteins is eliminated. In addition, problems related to degradation and loss of protein activity are eliminated by using recombinant cells to express the protein at the site. The use of recombinant cells to express the desired protein additionally results in the use of smaller amounts of proteins and increased graft success. Additionally, the recombinant cells can be engineered to have inducible expression of the proteins, so that protein expression can be turned on and off in vivo as necessary.

Second, seeding the prosthetic implant on an outer surface of the implant (e.g., the perivascular surface) where the graft is not in direct contact with blood flow eliminates the complications associated with denudation due to blood shear stresses on cells which are seeded on the inner, or lumenal surface of such implants. As discussed in the Background section above, researchers have focused intently on a variety of methods for seeding vascular grafts with endothelial cells to enhance the rate of graft healing and endothelialization. The prosthetic graft of the present invention eliminates the need to expend the considerable time and effort on interlumenal endothelial seeding and/or other complex processes associated with the use of endothelial cells, which can involve extensive manipulation of the graft and in many cases, still meets with only limited success.

Third, the use of the recombinant adherent cells according to the present invention not only eliminates the need to seed the lumenal surface of the implant with proteins or endothelial cells, but the adherence of the cells to the outer surface of the implant allows the graft to be easily manipulated ex vivo and in vivo, without the need for the use of additional devices or other extraneous binding compounds to contain the cells at the graft site. In a non-graft medical procedure for the repair of damaged physiological tubular structures, it has been proposed to introduce proteins or cells at an extralumenal site adjacent to a lesion in the damaged physiological tubular structure for diffusion of proteins into the damaged tissue (See for example, U.S. Pat. No. 5,540,928 to Edelman et al., U.S. Pat. No. 5,455,039 to Edelman et al., U.S. Pat. No. 5,527,532 to Edelman et al., U.S. Pat. No. 5,766,584 to Edelman). Such methods, however, require the use of additional matrices, devices, sheaths and/or binding agents to deliver and maintain the cells or proteins at the extralumenal surface of the damaged vessel to be repaired, and are therefore undesirable for use in the prosthetic graft of the present invention. Additionally, devices such as controlled release or wicking devices are required to provide a source by which such proteins can be continuously administered to the graft over a period of time sufficient to obtain a biological effect at the lumenal surface of the graft, adding yet another level of complexity to the delivery of proteins.

In contrast, the prosthetic graft of the present invention is essentially self-sufficient in that once the graft is prepared and implanted, there is no need for additional manipulation of the graft or renewed provision of cells or proteins at the graft site. The prosthetic graft of the present invention can therefore perform over extended periods of time without further surgical intervention. In addition, adherent cells suitable for use in the graft of the present invention can be transfected and cultured, the protein expression can be verified, the protein expression levels can be adjusted, and the cells can be applied and cultured on the prosthetic graft, with all such steps being accomplished ex vivo, prior to implantation of the graft into the host.

Fourth, the adherent cells useful in the present prosthetic graft are superior to the relatively non-adherent endothelial cells which have previously been used to seed vascular grafts, including recombinant endothelial cells. More particularly, suitable adherent cells for use in the present invention, which can include fibroblasts, mesenchymal stem cells, bone marrow stem cells (e.g., undifferentiated stem cells from adult bone marrow), embryonal stem cells, adipocytes, keratinocytes, vascular smooth muscle cells, platelets, and other cells which have been genetically engineered to be adherent, are all relatively easy to obtain as autologous cells from the patient in need of the graft and/or are relatively non-immunogenic (i.e., embryonal stem cells). For example, fibroblasts and keratinocytes can be obtained through non-invasive harvesting methods such as a skin biopsy punch, and platelets can be obtained through a simple blood draw. Adipocytes can be obtained by relatively non-invasive skin biopsy or liposuction. In contrast, endothelial cells must be harvested from an isolated blood vessel. As discussed above, obtaining a blood vessel from a patient requires additional surgery and can also lead to complications and discomfort for the patient. Additionally, embryonal and mesenchymal stem cells, which can be maintained as recombinant cells lines, are relatively non-immunogenic and therefore would eliminate the need to use autologous cells in the graft.

Moreover, suitable adherent cells for use in the present invention, and particularly fibroblast cells, are a much heartier cell type than endothelial cells and they grow and maintain their phenotype much better than endothelial cells in vitro. In particular, fibroblasts are relatively innocuous in terms of endogenous protein expression, and therefore, they make ideal host cells for the expression of heterologous proteins. Finally, embryonal stem cells, bone marrow stem cells and mesenchymal stem cells have the additional advantage that such cells can be induced to differentiate into a desired cell type and thereby endogenously produce certain proteins by addition of exogenous growth factors.

According to the present invention, a "prosthetic graft" is defined as an artificial substitute organ or tissue used for implantation/transplantation, and in the present invention, the prosthetic graft is used for the bypass, replacement or repair of an organ or tissue that contains blood flow in vivo. A prosthetic graft of the present invention includes at least two components: (1) a porous prosthetic implant for containing blood in vivo; and, (2) adherent cells adhered to an outer surface of the implant, whereby the cells are transfected with at least one recombinant nucleic acid molecule that encodes one or more proteins that enhance patency of the implant. Therefore, reference herein to the prosthetic graft is intended to encompass both the prosthetic implant itself and the adherent cells, and reference to the prosthetic implant is intended to reference only the portion of the graft which is the structural prosthesis for containment of blood flow. As used herein, to "contain blood flow" or "configured for containment of blood flow" means that the implant portion of the graft is configured to be a vessel, chamber, or other such structure that has or partially defines an interior space that confines and directs the flow of blood into, through and out of the graft. In a preferred embodiment, the prosthetic graft of the present invention is used to repair, replace or bypass a blood vessel, a heart, a chamber of a heart, or is used for vascular access, such as a dialysis shunt. The prosthetic implant can therefore include, but is not limited to, a prosthetic vessel, an artificial heart, a left ventricle assist device, or a dialysis shunt.

As discussed above, the prosthetic implant has an outer surface and an inner surface. The outer surface (e.g., external surface) is defined herein as a surface of the implant which is not in contact with blood flow. In a prosthetic vessel implant, the outer surface is also referred to as the perivascular surface of the vessel implant. The inner surface (e.g., internal surface) is defined herein as a surface of the implant which is in contact with blood flow. The inner surface of a prosthetic vessel implant can also be referred to as the lumenal surface. The inner surface defines an interior space enclosed by the implant through which blood can flow. The inner surface, or lumenal surface, of the implant is the surface upon which neovascularization events, such as endothelialization of the graft, and other events related to improved patency, such as inhibition of smooth muscle proliferation, occur.

According to the present invention, improved or enhanced patency is defined to encompass enhancement (i.e., increase, improvement) of any of the biological processes that contribute to the initiation, development, and/or maintenance of neovascularization of a blood-containing vessel or organ, as well as inhibition (i.e., decrease, diminution) of any of the biological processes that contribute to occlusion (i.e., closing, blocking off, obstruction of a vessel or organ), intimal hyperplasia (i.e., an increase in thickness of intimal tissue due to an increase in the number of its constituent cells) and/or failure of a blood-containing vessel or organ. As such, the term "enhanced patency" or "improved patency" can be used to generally refer to events which include: enhanced angiogenesis (i.e., blood vessel formation) in the vascular bed downstream of the prosthetic graft, enhanced angiogenesis transmurally and into the interior space of the prosthetic implant to endothelialize (i.e., attract, grow and establish endothelial cells) the inner surface of the prosthetic implant, inhibition of thrombosis, and inhibition of smooth muscle migration and/or proliferation.

According to the present invention, neovascularization includes any of the biological processes involved in the development and maintenance of a natural vessel or organ through which blood flows. More particularly, neovascularization results in the attraction, growth and establishment within the porous prosthetic implant of cells and tissue that are substantially similar to the natural tissue that defines blood vessels and/or the walls of a heart, for example. By "substantially similar" tissue, it is intended that the new cells and tissue formed on and within the implant be similar enough in composition, cellular/tissue organization and function to the naturally occurring tissue which is being repaired, replaced or bypassed, that the new tissue is capable of effectively performing the functions of the naturally occurring tissue in the graft recipient under normal physiological conditions. In particular, formation of a substantially natural new intimal surface (i.e., a neointima) is desirable in the prosthetic graft. A natural intimal surface primarily comprises a uniform covering of endothelial cells over which blood flows. Under normal physiological conditions, blood flows over such a surface without forming thromboses, since endothelial cells have natural characteristics which inhibit thrombosis. Preferably, enhanced neovascularization of a prosthetic graft of the present invention includes one or more of the following processes: angiogenesis (i.e., blood vessel formation) in the vascular bed downstream of the prosthetic graft and angiogenesis transmurally and into the interior space of the prosthetic implant to endothelialize (i.e., attract, grow and establish endothelial cells) the inner surface of the prosthetic implant.

As used herein, the ability of a protein to "enhance neovascularization" refers to the ability of the protein to initiate, regulate, provide and/or contribute to any process involved in successful neovascularization as described above, as well as the ability to enhance (i.e., increase, upregulate) any naturally occurring neovascularization which is occurring in the absence of the protein.

Preferably, inhibition of: occlusion, intimal hyperplasia and/or failure of a graft includes one or more of the following processes: inhibition of thrombosis, enhancement of thrombolysis, and/or inhibition of smooth muscle migration and/or proliferation.

The prosthetic implant of the present invention is porous to allow the protein(s) that are expressed and secreted by the adherent cells to perfuse into and through the implant from the outer surface of the implant to the inner surface of the implant, where inhibition of events that decrease patency and enhancement of events that increase patency (e.g., neovascularization of the implant, including endothelialization of the inner surface of the implant), can occur. In this fashion, the prosthetic implant of the present invention effectively serves, in part, as a delivery system for biological compounds. The size of the pores of the implant can be any minimal size which allows the passage of proteins therethrough, and any maximal size which maintains the mechanical properties of the graft (e.g., support, configuration). Preferably, the size of the pores of the implant are from about 0.1 $\mu$m to about 500 $\mu$m, and more preferably, from about 0.2 $\mu$m to about 100 $\mu$m.

The porous prosthetic implant for use in the prosthetic graft of the present invention can be constructed of any material that is porous and suitable for use in a prosthesis for the containment of blood flow in vivo. The material(s) can be biological (i.e., natural), synthetic, or combinations thereof. Preferably, the material(s) are non-immunogenic and/or non-calcific. Such materials include, but are not limited to, highly resilient polyester, expanded polytetrafluorethylene (ePTFE), high porosity ePTFE, non-immunogenic xenogeneic tissue (e.g., dye-mediated, cross-linked collagen), porous silicon rubber, porous polyurethane, porous degradable polymer and/or porous copolymers.

In one embodiment of the present invention, a prosthetic implant suitable for use in a prosthetic graft of the present invention is a small bore prosthetic vessel. The present invention is particularly valuable for use in replacement and repair of small bore vessels, because the graft eliminates problems with occlusion and hyperplasia which have previously made the use of non-autologous and non-biological small bore grafts difficult if not impossible. A small bore graft which does not require the harvesting of autologous vessels would be a less traumatic option for the patient and also provide an option for those patients with no suitable vessels. According to the present invention, a small bore graft is defined as a vessel with an inner diameter of less than about 6 mm. The present invention is also useful for prosthetic implant that is a medium or large bore vessel. A medium bore vessel is defined herein as a vessel with an inner diameter of from about 6 mm to about 12 mm, and a large bore vessel is defined herein as a vessel with an inner diameter of from about 12 mm to about 38 mm. A prosthetic vessel implant of the present invention can be used for any suitable purpose, including arterial or venous replacement, or as a dialysis shunt.

Accordingly, in one embodiment of the present invention, the prosthetic graft is a vascular graft which includes: (a) a porous prosthetic vessel having a perivascular surface and a lumenal surface; and (b) adherent cells adhered to the perivascular surface of the porous prosthetic vessel, wherein the adherent cells are transfected with a recombinant nucleic acid molecule operatively linked to a transcription control sequence. The recombinant nucleic acid molecule encodes a protein that enhances patency of the prosthetic vessel.

The prosthetic graft of the present invention also includes adherent cells adhered to the outer surface of the prosthetic implant. The adherent cells are transfected with at least one recombinant nucleic acid molecule operatively linked to a transcription control sequence. Each recombinant nucleic acid molecule encodes one or more proteins that enhance patency of the prosthetic implant.

According to the present invention, an adherent cell is any cell that naturally adheres to a surface in the absence of factors or conditions which inhibit the adhesive properties of the cell (i.e., under normal conditions), or that can be induced to be adherent. More particularly, an adherent cell is characterized herein as a cell that is capable of adhering to a surface of a prosthetic implant as described herein under in vitro and/or in vivo culture conditions that are suitable for the normal growth and propagation of the given cell type, such adherence being capable of occurring without the assistance of additional exogenous "binding factors" (e.g., by polymeric compositions, collagen, fibronectin, fibrin, attachment peptides, laminin, etc.) to bind the cell to the surface (i.e., the adherence ability is a natural characteristic of the cell type). Such a naturally adherent cell can have the characteristic of being naturally non-adherent or adherent depending upon induction of the characteristic or upon placement of the cell in an appropriate environment. A suitable adherent cell for use in the present invention is capable of naturally adhering to the surface of an implant as described above, and is further capable of remaining adhered to the surface of the implant during normal in vitro culture manipulations, implantation procedures, and normal in vivo stresses that occur at the outer surface of the graft. Typically, at least about 60%, and preferably, at least about 70%, and more preferably, at least about 80%, and even more preferably, at least about 90% of the total number of adherent cells that are initially adhered to an implant outer surface remain adhered to the surface during such manipulations and procedures. Cells that have such characteristics are known in the art and include, but are not limited to, fibroblasts, mesenchymal stem cells, bone marrow stem cells, embryonal stem cells, adipocytes, keratinocytes, vascular smooth muscle cells, and platelets.

According to the present invention, an adherent cell can also include a cell that has been genetically modified to be adherent, such the adherency becomes a natural characteristic of the genetically modified cell. A genetically modified cell is a cell that has been modified (i.e., mutated or changed) within its genome and/or by recombinant technology (i.e., genetic engineering) from its normal (i.e., wild-type or naturally occurring) form. For example, an endothelial cell is not considered to be an adherent cell according to the present invention, unless such cell has been genetically modified to be more adherent than a naturally occurring endothelial cell, in which case such a genetically modified endothelial cell is encompassed by the present invention. As discussed above, one advantage of the present invention over previously described prosthetic grafts is that the use of adherent cells on the outer surface of the graft eliminates the need for additional devices, delivery vehicles or binders that complicate preparation and compatibility of the graft and which can compromise the viability and stability of the recombinant cells and proteins produced by the cells.

Preferred adherent cells for use in the present invention include, but are not limited to fibroblasts, mesenchymal stem cells, bone marrow stem cells, embryonal stem cells, adipocytes, keratinocytes, vascular smooth muscle cells, platelets, and cells which have been genetically engineered to be adherent, with fibroblasts being particularly preferred.

The adherent cells of the present invention are transfected with at least one recombinant nucleic acid molecule that encodes one or more proteins that enhance patency in the prosthetic implant. Enhanced patency has been previously defined herein. According to the present invention, proteins that are particularly useful in enhancing patency in the prosthetic graft of the present invention include: a protein that enhances angiogenesis in the vascular bed downstream of the prosthetic graft, a protein that enhances angiogenesis transmurally and into the interior space of the prosthetic implant to endothelialize the inner surface of the prosthetic implant, a protein that inhibits thrombosis, a protein that causes thrombolysis, a protein that inhibits smooth muscle migration and/or proliferation, and/or a vasodilator protein.

Examples of proteins which are angiogenic (i.e., enhance or initiate angiogenesis) and/or are useful growth factors for enhancing patency include, but are not limited to: vascular endothelial growth factor (VEGF), platelet-induced growth factor (PlGF), transforming growth factor β1 (TGFβ1), acidic fibroblast growth factor (aFGF), basic fibroblast growth factor (bFGF), transforming growth factor α (TGFα), epidermal growth factor, osteonectin, angiopoietin 1 (Ang1), Ang2, insulin-like growth factor (IGF), platelet-derived growth factor AA (PDGF-AA), PDGF-AB and PDGF-BB. Examples of proteins which are useful for inhibiting thrombosis and/or causing thrombolysis include, but are not limited to: tissue plasminogen activator (TPA), streptokinase, hirudin V, αv-βIII, and urokinase plasminogen activator (uPA). An example of a protein which is useful for inhibiting smooth muscle cell migration and/or proliferation includes, but is not limited to nitric oxide synthase (NO synthase). An example of a vasodilator protein includes, but is not limited to prostacyclin. Other suitable proteins which can perform the above-described functions or otherwise enhance patency will be known to those of skill in the art. In addition, the amino acid and nucleic acid sequences for these proteins are known and therefore, the proteins can be readily produced recombinantly by a host cell using recombinant technology that is well known in the art.

According to the present invention, in one embodiment, all of the adherent cells which are adhered to the outer surface of the prosthetic implant can be transfected with the same recombinant nucleic acid molecule(s), so that each cell expresses the same recombinant protein(s). In another embodiment, adherent cells expressing different recombinant nucleic acid molecule(s) can be combined and adhered to the same implant. As such, several different proteins can be expressed on the same implant, and the proportions of the various proteins can be controlled by the proportion of adherent cells expressing each protein that are adhered to the outer surface of the implant or by the level of expression of the respective proteins.

Similarly, a single adherent cell is transfected with at least one recombinant nucleic acid molecule, but it is within the scope of the present invention that a single adherent cell can be transformed with two or more different recombinant nucleic acid molecules, so that a single adherent cell can express one, two, or multiple recombinant proteins. A single adherent cell can also be transfected with a single recombinant nucleic acid molecule that expresses one, two or multiple proteins, which can be under the control of the same transcription control sequence, or under the control of different transcription control sequences. In the case of expression of two or more recombinant nucleic acid molecules, the expression levels of the different molecules can be independently regulated, by, for example, controlling the copy number of the different recombinant nucleic acid molecules or by using different promoters to express the different proteins. According to the present invention, reference to "one" or "a single" recombinant nucleic acid molecule is intended to refer to one type of molecule or one particular sequence, but it is not to be interpreted to mean that a single host cell contains only one copy number of the molecule. For example, a host cell that is transfected with a single recombinant nucleic acid molecule can have and express one or multiple copies of the same recombinant nucleic acid molecule. It is to be noted that the term "a" or "an" entity generally refers to one or more of that entity; for example, a protein refers to one or more proteins, or to at least one protein. As such, the terms "a" (or "an"), "one or more" and "at least one" can be used interchangeably herein. It is also to be noted that the terms "comprising", "including", and "having" can be used interchangeably.

An adherent cell suitable for use in the present invention is produced by transforming a host adherent cell with at least one recombinant nucleic acid molecule, each comprising one or more isolated nucleic acid sequences encoding a protein as described above and operatively linked to one or more transcription control sequences. The transcription control sequence(s) are typically contained within an expression vector. An expression vector is a DNA or RNA vector that is capable of transforming a host cell and of effecting expression of a specified nucleic acid molecule. Preferably, the expression vector is also capable of replicating within the host cell. In the present invention, expression vectors are typically plasmids, although any other expression vectors, such as retroviral vectors, are encompassed by the present invention. Expression vectors of the present invention include any vectors that function (i.e., direct gene expression) in an adherent host cell. Such a vector can contain nucleic acid sequences that are not naturally found adjacent to the isolated nucleic acid molecules to be inserted into the vector. The vectors can be used in the cloning, sequencing, and/or otherwise manipulating of nucleic acid molecules.

The phrase "operatively linked" refers to linking a nucleic acid molecule to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells useful in the prosthetic graft and method of the present invention. A variety of such transcription control sequences are known to those skilled in the art. Preferred transcription control sequences include those which function in mammalian cells and include mammalian and retroviral transcription control sequences. Even more preferred transcription control sequences include those which function in a cell type selected from the group consisting of fibroblasts, mesenchymal stem cells, bone marrow stem cells, embryonal stem cells, adipocytes, keratinocytes, vascular smooth muscle cells, and/or platelets.

In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA. There is no limit, other than a practical limit, on the maximal size of a nucleic acid molecule in that the nucleic acid molecule can include a portion of a gene; an entire gene, including regulatory and other untranslated regions of the gene; multiple genes; or portions thereof.

An isolated nucleic acid molecule useful in the present invention can be obtained from its natural source either as an entire (i.e., complete) gene or a portion thereof capable of forming a stable hybrid with that gene. An isolated nucleic acid molecule can also be produced using recombinant DNA technology (e.g., polymerase chain reaction (PCR) amplification, cloning) or chemical synthesis. Isolated nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications provide the desired effect within the microorganism.

An allelic variant of a gene having a given nucleic acid sequence is a gene that occurs at essentially the same locus (or loci) in the genome as the gene having the given nucleic acid sequence, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art.

A nucleic acid molecule homologue can be produced using a number of methods known to those skilled in the art (see, for example, Sambrook et al., ibid.). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

Knowing the nucleic acid sequences of certain nucleic acid molecules encoding proteins useful in the present invention allows one skilled in the art to, for example, (a) make copies of those nucleic acid molecules and/or (b) obtain nucleic acid molecules including at least a portion of such nucleic acid molecules (e.g., nucleic acid molecules including full-length genes, full-length coding regions, regulatory control sequences, truncated coding regions). Such nucleic acid molecules can be obtained in a variety of ways including traditional cloning techniques using oligonucleotide probes of to screen appropriate libraries or DNA and PCR amplification of appropriate libraries or DNA using oligonucleotide primers.

Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into the host cell chromosome, addition of vector stability sequences to plasmids, substitutions or modifications of transcription control signals (e.g., promoters, operators, enhancers), substitutions or modifications of translational control signals, modification of nucleic acid molecules of the present invention to correspond to the codon usage of the host cell, and deletion of sequences that destabilize transcripts. The activity of an expressed recombinant protein of the present invention may be improved by fragmenting, modifying, or derivatizing nucleic acid molecules encoding such a protein.

It is preferred that the nucleic acid molecule encoding protein according to the present invention be cloned under control of an artificial promoter. The promoter can be any suitable promoter that will provide a level of protein expression required to maintain a sufficient level of the protein at the graft site to enhance patency of the implant, and preferably, to complete neovascularization of the implant. Preferred promoters are inducible promoters, since it is desirable to be able to regulate the expression of the protein ex vivo and/or in vivo at the site of graft implantation. In one embodiment, the promoter is inducible in vivo, so that the prosthetic graft can be implanted at the desired site in vivo, and the protein production can be regulated as necessary to enhance patency. In this embodiment, the protein production can be terminated after a time has passed that is sufficient to establish vascularization and particularly, endothelialization of the implant, thereby eliminating any undesirable side effects that may be created by prolonged exposure of the graft recipient to the proteins. Preferably, an inducible promoter useful in the present invention is induced by administration of a compound that regulates the promoter to the graft recipient, such compound being administered in an amount and by a route effective to regulate transcription of the recombinant nucleic acid molecule in the adherent cells. Such a compound can include, but is not limited to, an antibiotic, a hormone, or a transcription factor. In another embodiment, instead of a compound, the inducible promoter can be activated by a treatment such as internal or external radiation (e.g., X-ray). Alternatively, a promoter may be selected that will be induced upon placement in the in vivo environment of the implant, by naturally occurring compounds (e.g., hormones) that enter or are produced by the adherent cells and bind to and induce the promoter.

The gene dosage (copy number) of a recombinant nucleic acid molecule according to the present invention can also be varied according to the requirements for maximum product formation. In one embodiment, the recombinant nucleic acid molecule encoding a protein useful in the present invention is integrated into the chromosome of the host cell.

Proteins expressed by recombinant nucleic acid molecules according to the present invention are secreted from the cell. Therefore, recombinant nucleic acid molecules used in the present invention typically contain secretory signals (i.e., signal segment nucleic acid sequences) to enable an expressed protein of the present invention to be secreted from the cell that produces the protein. Examples of suitable signal segments include any signal segment capable of directing the secretion of a protein of the present invention. Preferred signal segments include signal segments which are naturally associated with the expressed protein, when such protein is a secreted protein, but can include any signal segment that functions in a host cell according to the present invention.

A protein that enhances patency produced by a recombinant nucleic acid molecule according to the present invention includes can be a full-length protein (i.e., in its full-length, naturally occurring form), any homologue of such a protein, any fusion protein containing such a protein, or any mimetope of such a protein. The amino acid sequences for many patency enhancing proteins disclosed herein, as well as nucleic acid sequences encoding the same, are known in the art and are publicly available, for example, from sequence databases such as GenBank. Such sequences can therefore be obtained and used to produce proteins and recombinant nucleic acid molecules of the present invention.

A homologue is defined as a protein in which amino acids have been deleted (e.g., a truncated version of the protein, such as a peptide or fragment), inserted, inverted, substituted and/or derivatized (e.g., by glycosylation, phosphorylation, acetylation, myristoylation, prenylation, palmitation, amidation and/or addition of glycosylphosphatidyl inositol). A homologue of a given protein is a protein having an amino acid sequence that is sufficiently similar to a naturally occurring protein amino acid sequence that the homologue has substantially the same, or enhanced or even reduced biological activity compared to the corresponding naturally occurring protein.

As used herein, a mimetope (also referred to as a synthetic mimic) of a protein that enhances patency according to the present invention refers to any compound that is able to mimic the activity of such a protein, often because the mimetope has a structure that mimics the protein. Mimetopes can be, but are not limited to: peptides that have been modified to decrease their susceptibility to degradation; anti-idiotypic and/or catalytic antibodies, or fragments thereof; non-proteinaceous immunogenic portions of an isolated protein (e.g., carbohydrate structures); and synthetic or natural organic molecules, including nucleic acids. Such mimetopes can be designed using computer-generated structures of the naturally occurring protein. Mimetopes can also be obtained by generating random samples of molecules, such as oligonucleotides, peptides or other organic or inorganic molecules, and screening such samples by affinity chromatography techniques using the corresponding binding partner.

According to the present invention, a fusion protein is a protein that includes a patency-enhancing protein containing domain attached to one or more fusion segments. Suitable fusion segments for use with the present invention include, but are not limited to, segments that can: enhance a protein's stability; enhance the biological activity of a patency-enhancing protein; and/or assist purification of a patency-enhancing protein (e.g., by affinity chromatography). A suitable fusion segment can be a domain of any size that has the desired function (e.g., imparts increased stability, imparts enhanced biological activity to a protein, and/or simplifies purification of a protein). Fusion segments can be joined to amino and/or carboxyl termini of the patency-enhancing protein-containing domain of the protein and can be susceptible to cleavage in order to enable straight-forward recovery of a patency-enhancing protein, if such recovery is desired. Fusion proteins are preferably produced by culturing a recombinant cell transformed with a fusion nucleic acid molecule that encodes a protein including the fusion segment attached to either the carboxyl and/or amino terminal end of a patency-enhancing protein-containing domain. Preferred fusion segments include a metal binding domain (e.g., a poly-histidine segment); an immunoglobulin binding domain (e.g., Protein a; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies).

Suitable host cells to transform include any adherent cell as described above that can be transformed with a nucleic acid molecule encoding a protein useful in the prosthetic graft of the present invention. Host cells can be either untransformed adherent cells or cells that are already transformed with at least one nucleic acid molecule (e.g., nucleic acid molecules encoding one or more proteins useful in the present invention). Adherent host cells of the present invention can be endogenously (i.e., naturally) capable of producing the useful proteins of the present invention in addition to being capable of producing such proteins after being transformed with at least one recombinant nucleic acid molecule encoding such protein.

Suitable adherent host cells can be obtained from the recipient of the prosthetic graft of the present invention (i.e., autologous cells), from a histocompatible allogeneic donor, from a xenogeneic donor, from an embryonal cell source, and/or from established cell lines that are propagated in vitro. Methods of obtaining and culturing autologous cells from the graft recipient or allogeneic/xenogeneic cells from a donor vary depending on the type of cell to be obtained, and are well known in the art. For example, methods for obtaining and culturing fibroblasts and other cells from a donor are described in detail in U.S. Pat. No. 5,460,959, to Mulligan et al.; R. Ian Feshney, *Culture of Animal Cells*, Editor: Wiley-Liss, 3rd ed., 1994; Paw and Zon, 1999, *Methods Cell Biol* 59:39–43; and Hodges-Garcia et al., 1998, *In Vitro Cell Dev Biol Anim* 34(5):364–366; each of which is incorporated herein by reference in its entirety.

Transformation of a nucleic acid molecule into a cell can be accomplished by any method by which a nucleic acid molecule can be inserted into the cell. Transformation techniques include, but are not limited to, transfection, electroporation and microinjection. Methods of transducing fibroblasts for expression of heterologous proteins are described in detail in U.S. Pat. No. 5,460,959, ibid.; and Ray and Gage, 1992, *Biotechniques* 13(4):598–603, incorporated herein by reference in its entirety.

Proteins which enhance patency are expressed and secreted from adherent host cells of the present invention by culturing the recombinant adherent cell capable of expressing the protein under conditions effective to produce the protein. Such conditions include both ex vivo and in vivo conditions. Effective ex vivo culture conditions include, but are not limited to, effective media, bioreactor, temperature, pH and oxygen conditions that permit protein production. An effective medium refers to any medium in which a cell is cultured to produce protein according to the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. An example of suitable culture conditions is described in the Examples section. Effective in vivo conditions are normal physiological conditions at the site of the implantation of the prosthetic graft. Additionally, effective in vivo conditions can include the presence of a promoter inducer, if the transcription control sequence of the recombinant nucleic acid molecule includes an inducible promoter.

Prior to, or after adhering an adherent cell of the present invention to a prosthetic implant as described herein, the expression of the desired recombinant protein by the recombinant adherent cell can be verified by a method such as, but not limited to, immunoblot or analysis of the biological activity of the protein to be expressed. If necessary, the expression level of the protein can be adjusted by methods which include, but are not limited to, recloning the nucleic acid molecule into a higher copy number plasmid, integration of the nucleic acid molecules into the host cell chromosome, addition of vector stability sequences to plasmids, substitutions or modifications of transcription control signals (e.g., promoters, operators, enhancers), substitutions or modifications of translational control signals, modification of nucleic acid molecules to correspond to the codon usage of the host cell, and deletion of sequences that destabilize transcripts, etc.

Recombinant adherent cells of the present invention are grown in vitro in effective culture conditions for an amount of time effective to establish a sufficient number of viable recombinant cells to adhere to a prosthetic implant to be implanted into a patient. The number of cells that is sufficient to adhere to a prosthetic implant will vary depending on the size and shape of the implant, and depending on the amount of protein expressed per cell. In general, a prosthetic implant should be seeded on the outer surface with a number of cells sufficient to express an amount of protein that can diffuse into the graft, and, under in vivo conditions including blood shear forces, within the implant and at the inner surface of the graft, effect the desired biological activity. Determination of these parameters is well within the ability of one of ordinary skill in the art and is described in detail in the Examples section.

In one embodiment of the method of the present invention, a recombinant nucleic acid molecule encoding a protein that enhances patency as described above is delivered to the outer surface of a prosthetic implant as described herein by a non-cellular delivery vehicle that adheres to the outer surface of the implant and/or perfuses into the pores of the implant. In this embodiment, instead of using an adherent cell to express and deliver the protein to the implant, a non-cellular vehicle, including, but not limited to: a liposome, an immunoliposome, or a controlled release polymer delivery vehicle, is used to deliver the protein onto the outer surface of the implant. Upon implantation, the liposome can transfect host cells in the vicinity of the outer surface of the graft or which are recruited to the graft with the recombinant nucleic acid molecule, whereby the recombinant nucleic acid molecule is expressed by the cells.

A liposome delivery vehicle of the present invention comprises a lipid composition that is capable of fusing with the plasma membrane of a cell to deliver a nucleic acid molecule or other compound into a cell. An immunoliposome is a liposome which requires an antibody (conjugated to a lipid anchor) not only for specific target cell recognition but also as stabilizer of the otherwise unstable liposome (Ho et al., 1986, *Biochemistry* 25: 5500–6; Ho et al., 1987a, *J Biol Chem* 262: 13979–84; and Ho et al., 1987b, *J Biol Chem* 262: 13973–8; all incorporated herein by reference in their entireties). Suitable liposomes for use with the present invention include any liposome. Preferred liposomes of the present invention include those liposomes commonly used in, for example, gene delivery methods known to those of skill in the art. Complexing a liposome with a nucleic acid molecule of the present invention can be achieved using methods standard in the art. A suitable concentration of a nucleic acid molecule of the present invention to add to a liposome includes a concentration effective for delivering a sufficient amount of nucleic acid molecule into a host cell such that the protein is expressed at a level sufficient to enhance patency in the graft, including at the inner surface of the graft.

Vehicles for non-cellular delivery of a recombinant nucleic acid molecule encoding a protein that enhances patency as described above also include a controlled release formulation that is capable of slowly releasing the recombinant nucleic acid molecule into the graft site. As used herein, a controlled release formulation comprises a recombinant nucleic acid molecule encoding a protein that enhances patency in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposphere, and transdermal delivery systems. Other controlled release formulations of the present invention include liquids that, upon association with the prosthetic implant, form a solid or a gel in situ. Such controlled release vehicles are preferably associated with the prosthetic implant by one of the above-described methods. Preferred controlled release formulations are biodegradable (i.e., bioerodible).

One embodiment of the present invention relates to a method for producing a prosthetic graft. Such a method comprises applying adherent cells to a porous prosthetic implant for containing blood in vivo, wherein the prosthetic implant has an outer surface and an inner surface that defines an interior space for containment of blood flow. The adherent cells are applied to the outer surface of the prosthetic implant. As described above, the adherent cells are transformed with at least one recombinant nucleic acid molecule operatively linked to a transcription control sequence, the recombinant nucleic acid molecule encoding a protein that enhances patency of the prosthetic implant.

Preferably, the adherent cells are seeded (i.e., applied) onto the outer surface of the prosthetic implant so that they are uniformly dispersed on the surface of the implant (e.g., both radially and longitudinally, if the implant is a vessel). Such a uniform seeding has been demonstrated by the present inventors to be sufficient to obtain the desired protein production in vivo under blood shear stress conditions. In one embodiment, the number of cells seeded onto the outer surface of a prosthetic implant is from about 1500 cells to about 4000 cells per $mm^2$ surface area of the implant, and preferably, from about 2000 to about 3500 cells per $mm^2$ surface area of the implant, and even more preferably from about 2500 to about 3000 cells per $mm^2$ surface area of the implant. In another embodiment, the cells are seeded so that from about 0.5 fg to about 500 pg of each recombinant protein is secreted per ml per $mm^2$ surface area of the implant. In one embodiment, the cells are seeded so that from about 0.5 fg to about 20 fg of each recombinant protein is secreted per ml per $mm^2$ surface area of the implant, and preferably, from about 1 fg to about 15 fg of each recombinant protein is secreted per ml per $mm^2$ surface area of the implant. In another embodiment, the cells are seeded so that from about 1 pg to about 500 pg of each recombinant protein is secreted per ml per $mm^2$ surface area of the implant, and preferably, from about 10 pg to about 300 pg of each recombinant protein is secreted per ml per $mm^2$ surface area of the implant.

The prosthetic implant can be seeded with the adherent cells by any method which allows the cells to naturally adhere to the implant (i.e., without the need for exogenously added binding agents, sheaths or other devices), and which maintains cell viability and the ability of the cells to effectively express the protein. In one embodiment, the implant is seeded by applying cells to the implant on one side, rotating the implant about 90°, seeding the next quadrant of the implant, and repeating the procedure until all sections of the implant have been seeded. The seeding can be performed manually, or using a programmable mechanical graft rotator. Since the cells are naturally adherent and will not be exposed to blood shear forces, it is not necessary to use complex forced seeding methods that have been previously described for endothelial cell seeding, although such methods can be used, if desired.

Following application of the adherent cells to the implant to produce the prosthetic graft of the present invention, the graft is typically incubated under effective cell culture conditions as described above for a short time to allow for adequate cell adhesion to the implant. The graft can then be maintained under effective cell culture conditions as described above until the graft is to be implanted into the recipient. The incubation period can be as short as about 5 minutes, or can be extended to at least about 14 days prior to implantation of the graft into the host. Yet another advantage of the graft of the present invention is that once the graft is prepared, it can be maintained in culture until such time as the recipient is ready for implantation.

Yet another embodiment of the invention relates to a prosthetic graft for containment of blood flow in vivo which includes: (a) a porous prosthetic implant for containing blood in vivo, having an outer surface that is not in contact with blood flow in vivo and an inner surface that is in contact with blood flow in vivo, whereby the inner surface defines an interior space for containment of blood flow; and, (b) adherent cells adhered to the outer surface of the porous prosthetic implant. In this embodiment, the adherent cells can include both: (a) adherent cells which are transfected with a recombinant nucleic acid molecule that encodes at least one protein that enhances patency of the prosthetic implant as described previously herein; and (b) adherent cells which naturally (i.e., endogenously) produce and secrete at least one protein that enhances patency of the prosthetic implant. As described above, an adherent cell includes cells that have been genetically modified (e.g., by mutation or recombinant technology) to be adherent. Therefore, in one aspect of this embodiment of the present invention, the adherent cells are endothelial cells that have been genetically modified to be adherent. Endothelial cells naturally express proteins that enhance patency of a prosthetic implant. As discussed above, an adherent cell is capable of adhering to the outer surface of prosthetic implant without the assistance of additional exogenous "binding factors". Other aspects of this embodiment of the present invention have been previously described herein as for the other embodiments of the present invention.

Another embodiment of the present invention is a method to implant a prosthetic graft for containment of blood flow into a patient in need of such a graft. The method includes the step of implanting into a recipient patient a prosthetic graft of the present invention, such graft being configured and prepared as described in detail above. In one embodiment of such a method, the method includes an initial step of harvesting adherent cells, preferably fibroblast cells, from the patient who is in need of a prosthetic graft for containing blood flow.

Preferably, the adherent cells used in the graft are autologous to the patient. If the adherent cells are autologous, the cells are harvested from the patient as discussed above, transfected with the desired recombinant nucleic acid molecules as described above, seeded onto the prosthetic implant as described above, and implanted into the patient. In one embodiment, the cells are selected from undifferentiated stem cell lines or embryonal cell lines. The cells can be induced to express the protein(s) which enhance patency either ex vivo, prior to implantation of the graft into the patient, or in vivo, after implantation of the graft into the patient.

The step of implantation of the prosthetic graft of the present invention into a patient is performed by any method which is suitable for implantation of such a graft. The surgical techniques for implantation of vascular grafts, artificial hearts, left ventricle assist devices, and dialysis shunts are well known and published in the art. Such methods are described, for example, in Persson and Griffey, 1980, *Surgical Clinics of North America* 60(3):527–535; Mannick, 1979, *Surgical Clinics of North America* 59(4):581–596, incorporated herein by reference in their entireties.

If the prosthetic graft of the present invention includes adherent cells that are transformed with recombinant nucleic acid molecules with inducible promoters, the patient is administered, either before, during, or after the implantation of the graft, a compound which induces the promoter to begin expression of the promoter at the outer surface of the prosthetic implant. Such compounds and promoters have been discussed previously herein. The compound can be administered in a pharmaceutically acceptable carrier which is capable of maintaining the compound in a form that, upon arrival of the compound at the graft site, the compound is biologically active such that induction of the promoter can occur. Examples of pharmaceutically acceptable carriers include, but are not limited to water, phosphate buffered saline, Ringer's solution, dextrose solution, serum-containing solutions, Hank's solution, other aqueous physiologically balanced solutions, oils, esters, glycols, polymeric controlled release vehicles, biodegradable implants, liposomes, bacteria, viruses and cells. Routes of administration can include, but are not limited to, oral, nasal, topical, transdermal, rectal, and parenteral routes. Parenteral routes can include, but are not limited to, subcutaneous, intradermal, intravenous, and intramuscular routes. The promoter-inducing compound can also be applied to the graft or at a site adjacent to the graft at the time of implantation.

The following examples are provided for the purposes of illustration and are not intended to limit the scope of the present invention.

EXAMPLES

Example 1

The following example describes the production of a prosthetic graft according to the present invention.

Primary Cell Culture:

Primary Rabbit Aortic Fibroblasts (RAF) were obtained from young male White New Zealand rabbits. The aorta was explanted, the vessel was then longitudinally opened and the endothelium was removed by gently rubbing the lumenal surface with a scraper. After this step, the vessel was cut into small pieces, it was placed in a 60 mm dish containing 2 ml of Trypsin and kept at 37° C. in a 5% $CO_2$ incubator for 60 minutes. After this incubation, the vessel was removed and placed in 60 mm dishes with 0.5 ml of DMEM supplemented with 10% FBS containing 2 mM L-glutamine and 100 UI/mL Pen/Strep. After overnight incubation, 1.5 ml of culture medium was added. RAFs were cultured with DMEM with 10% FBS, 2 mM L-glutamine and 100 UI/mL Pen/Strep in a humidified 5% $CO_2$ atmosphere at 37° C. Proliferating cells were used between passage 3 and 8 and were used for infection when they reached 70% confluence. Rabbit fibroblasts were used for the preliminary in vitro assays described in Examples 2–4.

In the in vivo assay described in Example 5, pig primary fibroblasts were obtained from pig rectus fascia according to the following procedure. While the animal is under general anesthesia, the abdomen is aseptically prepared and under sterile conditions, a 10 cm long longitudinal skin incision is made over the right rectus muscle. The fat under the skin is gently divided and the anterior fascia of the rectus muscle is exposed and cleaned of all fat tissue with a swab. The fascia is incised with a scalpel and a 5 cm×5 cm square of fascia is removed with scissors. Hemostasis is performed, the surgical incision is closed in 2 layers, and anesthesia is terminated. Adipocytes were removed from the excised tissue by a forceps under surgical microscopy and the fascia was cut in small pieces and digested with trypsin for 1 hour. After incubation, the pieces were then removed and placed in 60 mm dishes with 0.5 ml of DMEM supplemented with 10% FBS containing 2 mM L-glutamine and 100 UI/mL Pen/Strep. After overnight incubation, 1.5 ml of culture medium was added.

Cell Infection with Adenovirus:

A similar protocol was used to infect both rabbit and pig fibroblasts. The virus used for this experiment was an adenovirus coding for VEGF. Cells were cultured in complete DMEM until 70% confluence. Prior the infection, cells in one dish were harvested with trypsin and counted. Cells in the remaining dishes were infected with 200 pfu/cell and incubated in a humidified 5% $CO_2$ atmosphere at 37° C. for 90 minutes. The infected medium was replaced with D-MEM supplemented with 10% FBS complete, and cells were kept in incubator at 37° C. for 24 hours. To verify the infection efficiency, conditioned medium of infected cells and conditioned medium of uninfected cells was collected and VEGF analyzed in the medium was quantified with an ELISA assay commercially available from R&D performed according to standard procedures.

PhotoFix Preparation:

PhotoFix grafts stored in 50% ethanol were washed in PBS twice for fifteen minutes and twice for two hours in fresh PBS, then they were placed overnight at 4° C. in fresh PBS.

Seeding of PhotoFix:

After ethanol washing, the PhotoFix graft was cut in 5 cm pieces and seeded with infected cells at concentration of 1.25×10 cell/ml and two ml of suspension were used for seeding. After seeding on first quadrant, the PhotoFix was placed in a humidified 5% $CO_2$ atmosphere at 37° C. for 30 minutes, then the PhotoFix was seeded on second quadrant and placed in a humidified 5% $CO_2$ atmosphere at 37° C. for 30 minutes. The two other quadrants were seeded in the same way. At the end of this procedure the PhotoFix was incubated in a humidified 5% $CO_2$ atmosphere at 37° C. for 20 hours.

Example 2

The following example demonstrates that a prosthetic graft of the present invention produces the recombinant protein both inside and outside of the graft under static in vitro culture conditions.

Production and secretion of VEGF under static in vitro conditions was measured from the PhotoFix graft seeded perivascularly with rabbit aortic fibroblasts infected with AdV cmv VEGF as described in Example 1. Briefly, the seeded PhotoFix was mounted within a closed circuit placed in a chamber and connected to a peristaltic pump. Five ml of medium in static condition were placed inside the PhotoFix, while 300 ml of medium was placed in the incubation chamber outside the PhotoFix. The chamber was incubated under static conditions under shear stress in a humidified 5% $CO_2$ atmosphere at 37° C. At the end of incubation, external and internal medium was recovered (the internal medium was collected through a plastic outlet mounted on the circuit) and stored at −20° C. for the ELISA assay, while the graft was fixed, dehydrated, embedded in paraffin and sectioned for histologic analyses.

After two days of −20° C. incubation, VEGF production was measured by enzyme-linked immunosorbant assay (ELISA) at given times (0, 12, 24, 48, 72 hours) in the medium inside (internal) and outside (external) the graft. The ELISA used was a commercially available ELISA kit for VEGF from RND. For each time point, a different graft was used for the measurement. Negative and positive controls represent medium conditioned for 24 hours by uninfected fibroblasts or infected fibroblasts, respectively.

Figure 1B:
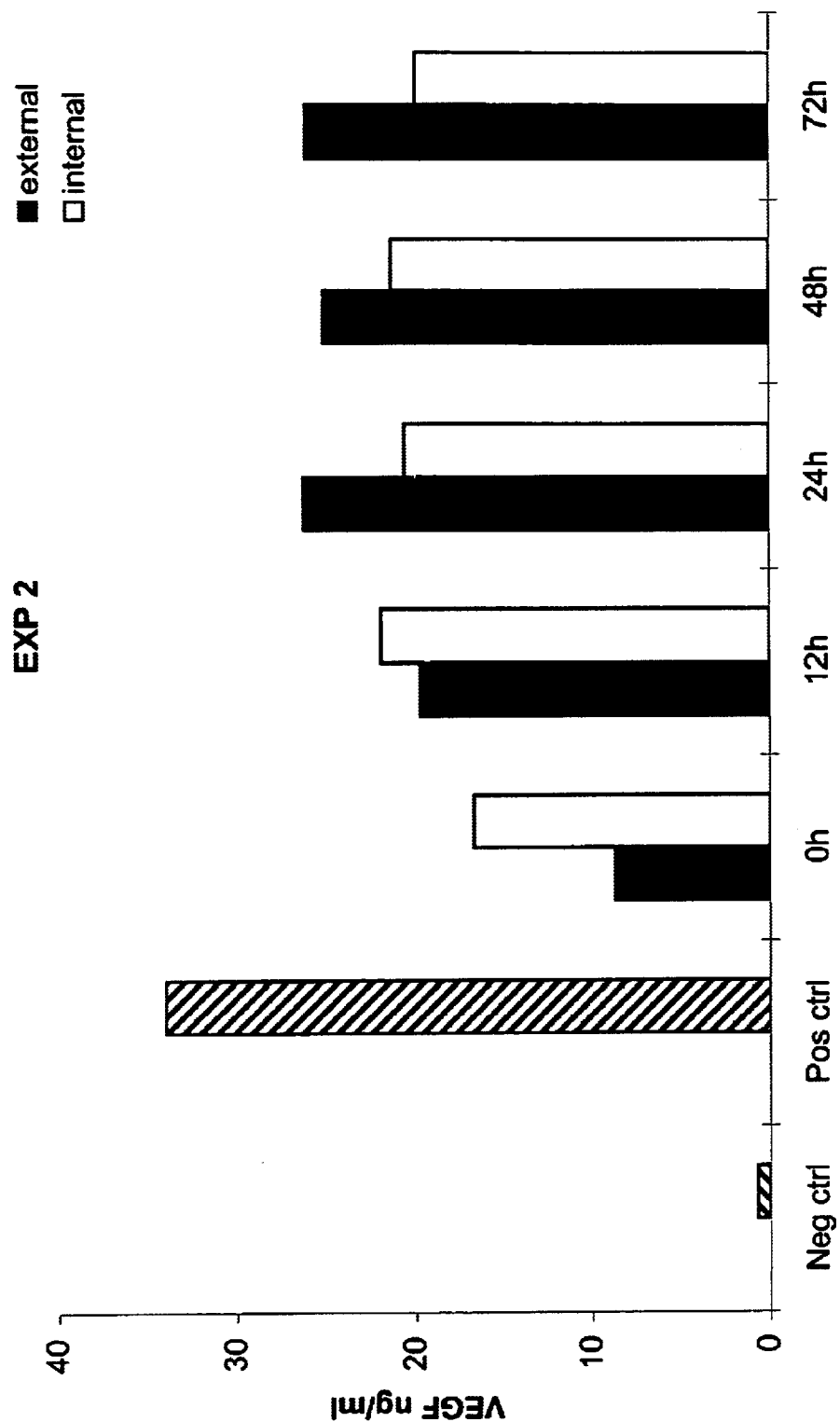
FIG. 1B is a bar graph showing the release of VEGF under static conditions by a prosthetic graft of the present invention.
Figure 1C:
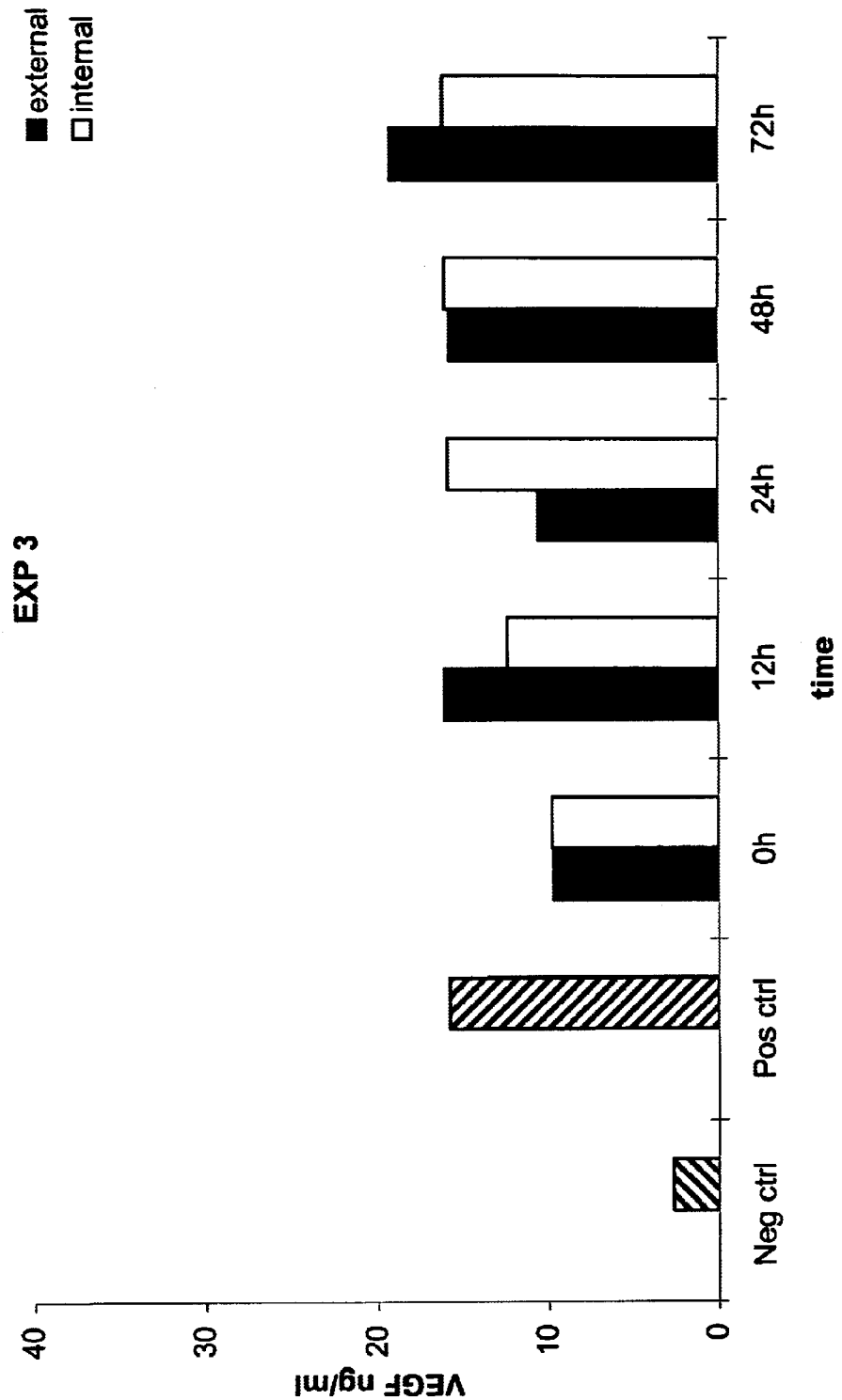
FIG. 1C is a bar graph showing the release of VEGF under static conditions by a prosthetic graft of the present invention.
Figure 1D:
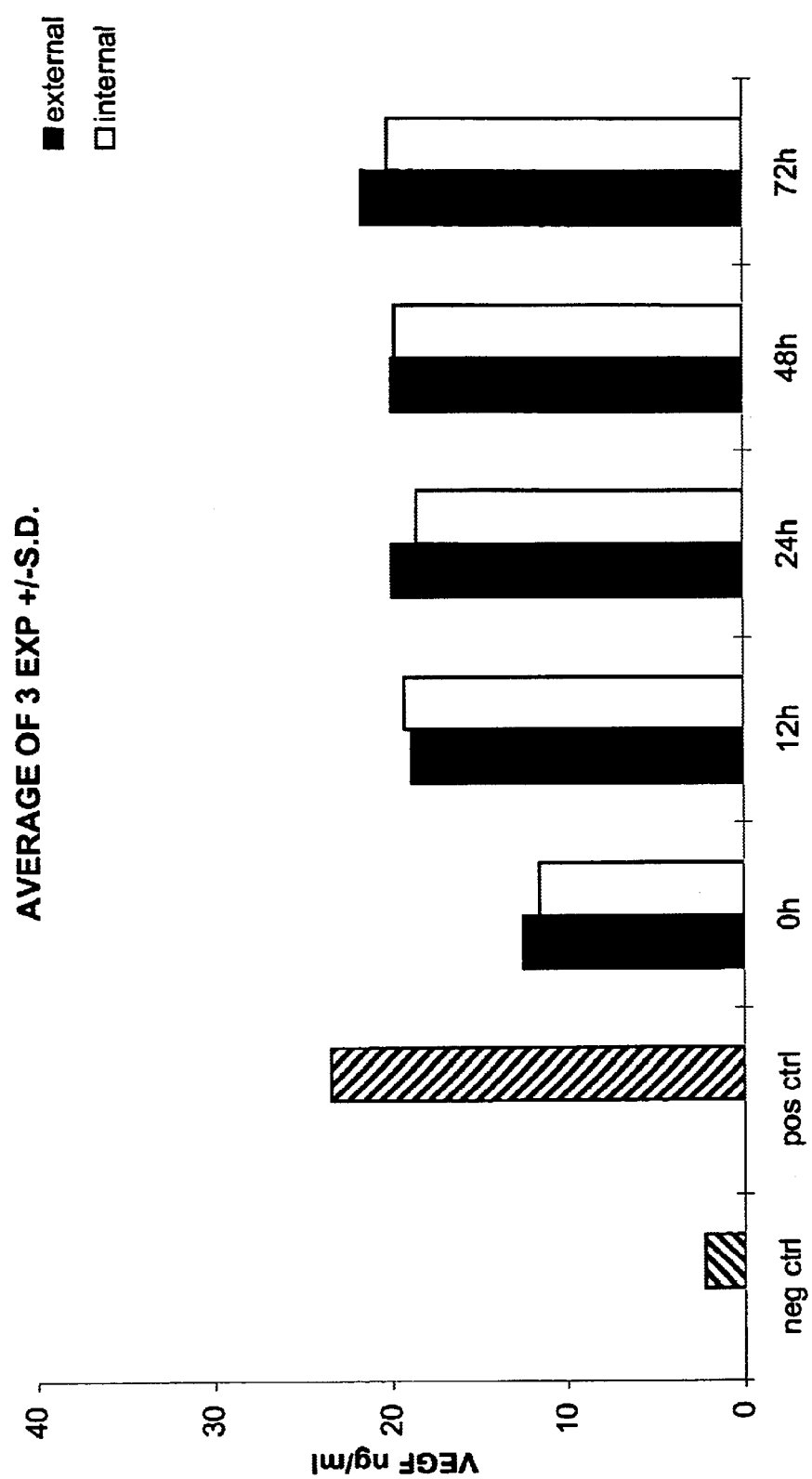
FIG. 1D is a bar graph showing the average release of VEGF under static conditions according to FIGS. 1A–1C by a prosthetic graft of the present invention.

The results of three separate experiments are illustrated in FIGS. 1A–1C. FIG. 1D is a composite graph representing the average results of all three experiments. FIGS. 1A–1D demonstrate that a prosthetic vessel graft of the present invention produces significant and comparable amounts of VEGF protein both outside the graft and inside the graft under in vitro static conditions.

Example 3

The following example demonstrates that a prosthetic graft of the present invention produces the recombinant protein both inside and outside of the graft under shear stress in vitro culture conditions.

Release of VEGF under dynamic condition-shear stress of 1.5 dyn/cm$^2$ during in vitro conditions was measured from the PhotoFix graft seeded perivascularly with rabbit aortic fibroblasts infected with AdV cmv VEGF as described in Example 1. Briefly, as described in Example 2 above, the seeded graft was mounted within a closed circuit placed in a chamber and connected to a peristaltic pump. For the dynamic condition assays, 15 ml of medium were placed inside the PhotoFix and 300 ml of medium was placed in the incubation chamber outside the PhotoFix. The chamber was incubated in a humidified 5% $CO_2$ atmosphere at 37° C. under dynamic conditions of shear stress by circulating the medium through the circuit at a velocity of 1.5 dyn/cm$^2$ as indicated. The medium was collected and tested for VEGF as described in Example 2.

VEGF production was measured by ELISA as described in Example 2 at given times (0, 4, 8, 12 hours) in the medium inside and outside the graft. For each time point, a different graft was used for the measurement. Negative and positive controls represent medium conditioned for 24 hours by uninfected fibroblasts or infected fibroblasts, respectively.

Figure 2A:
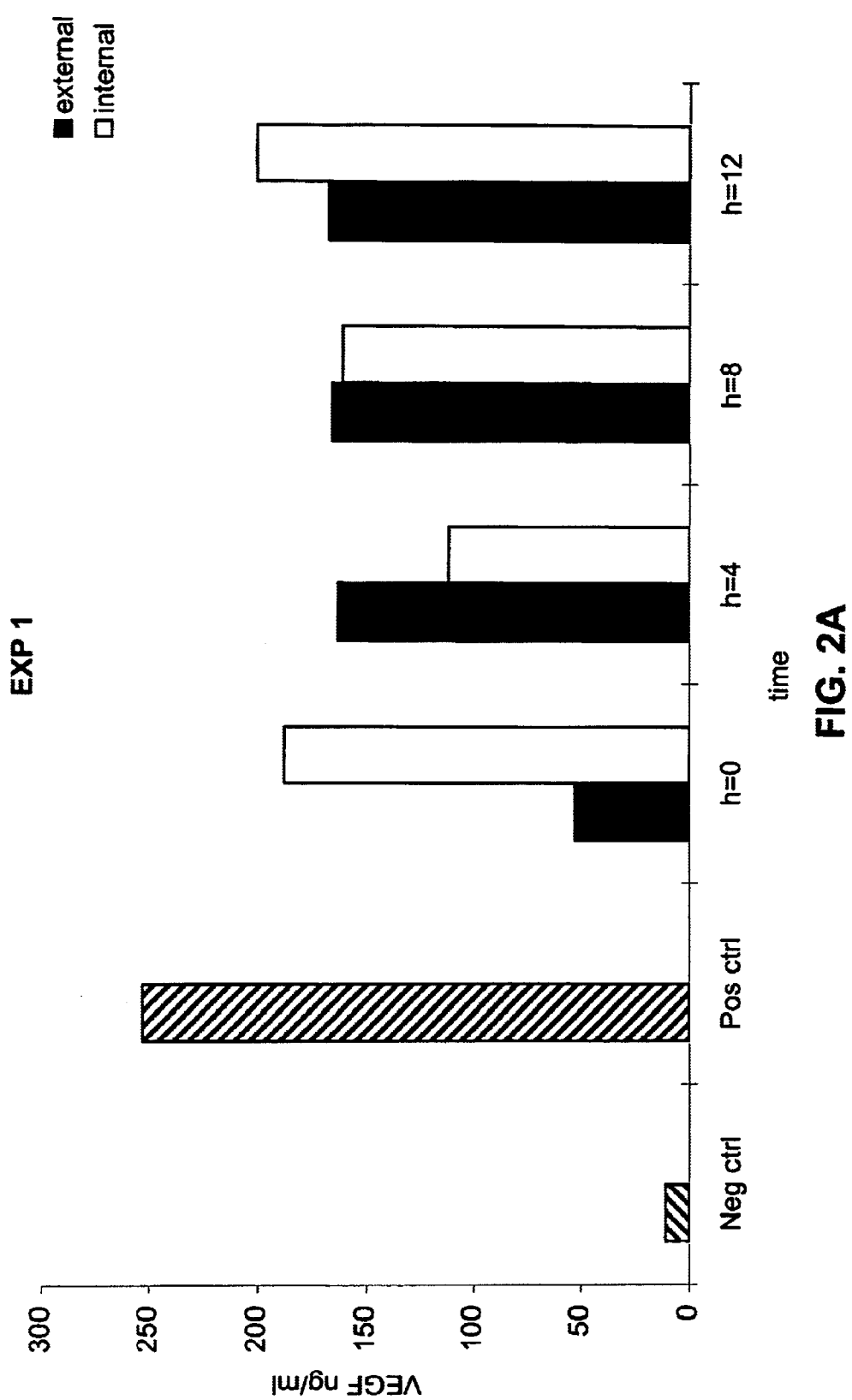
FIG. 2A is a bar graph showing the release of VEGF under shear stress of 1.5 $dyn/cm^2$ by a prosthetic graft of the present invention.
Figure 2B:
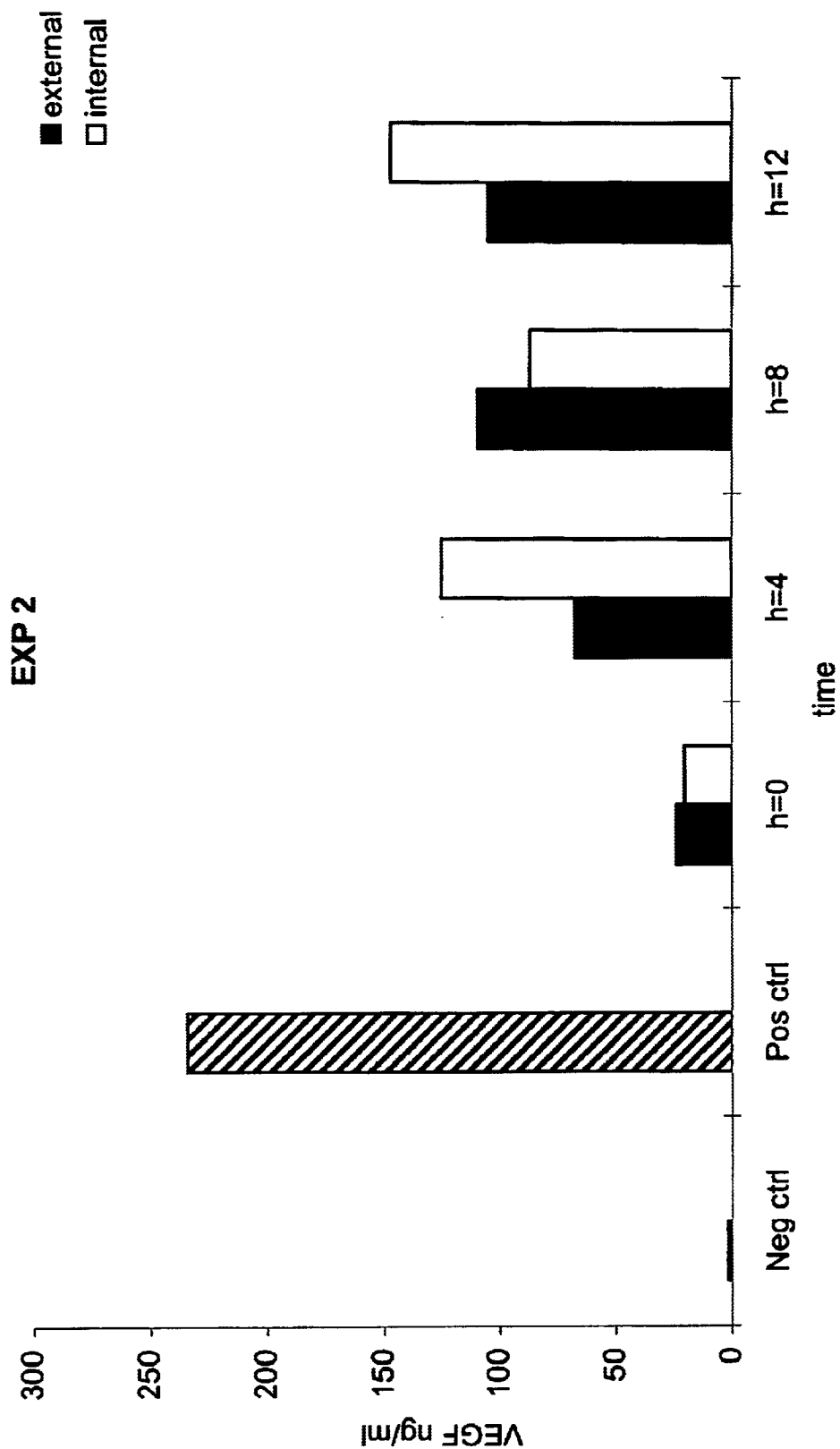
FIG. 2B is a bar graph showing the release of VEGF under shear stress of 1.5 $dyn/cm^2$ by a prosthetic graft of the present invention.
Figure 2C:
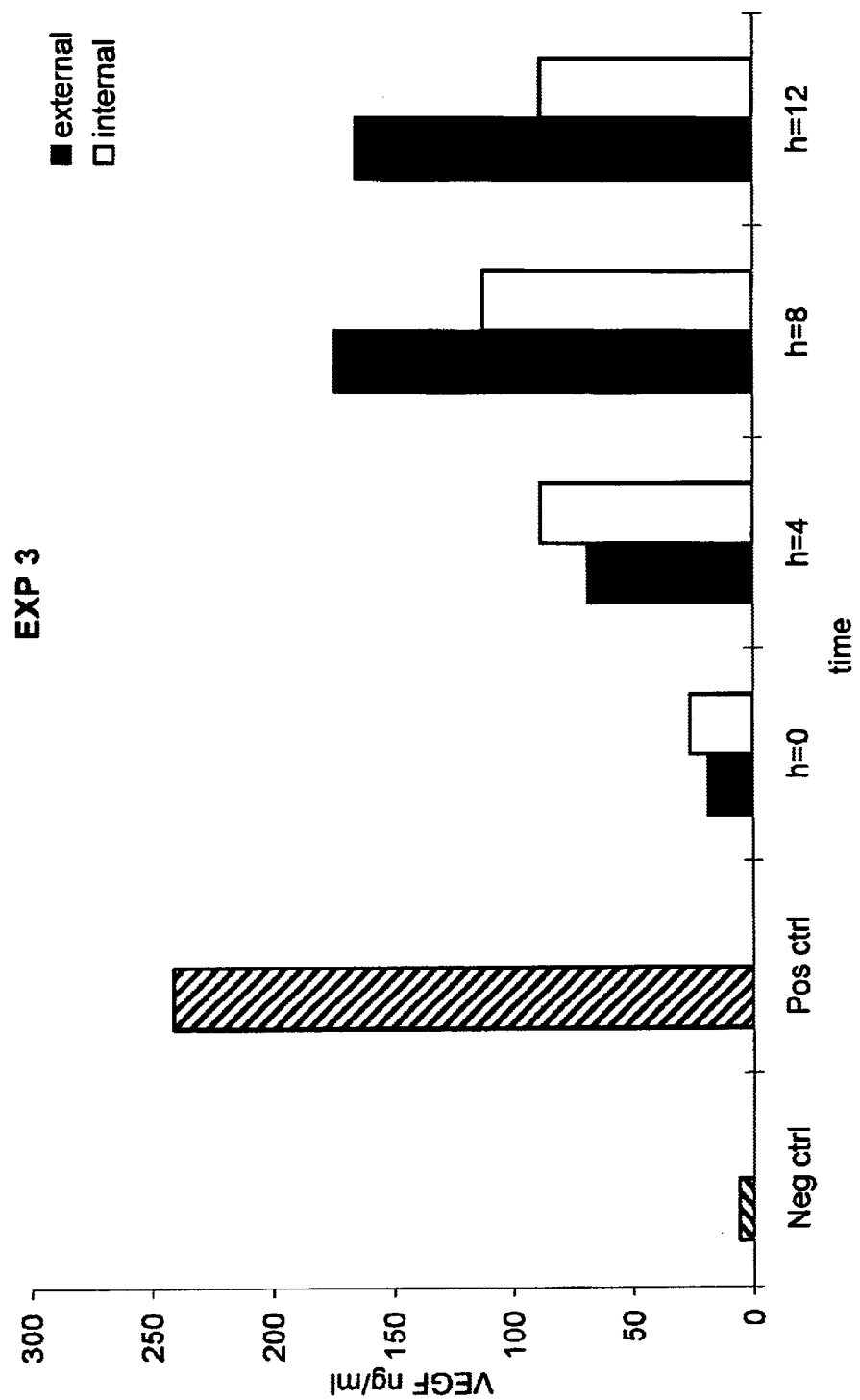
FIG. 2C is a bar graph showing the release of VEGF under shear stress of 1.5 $dyn/cm^2$ by a prosthetic graft of the present invention.
Figure 2D:
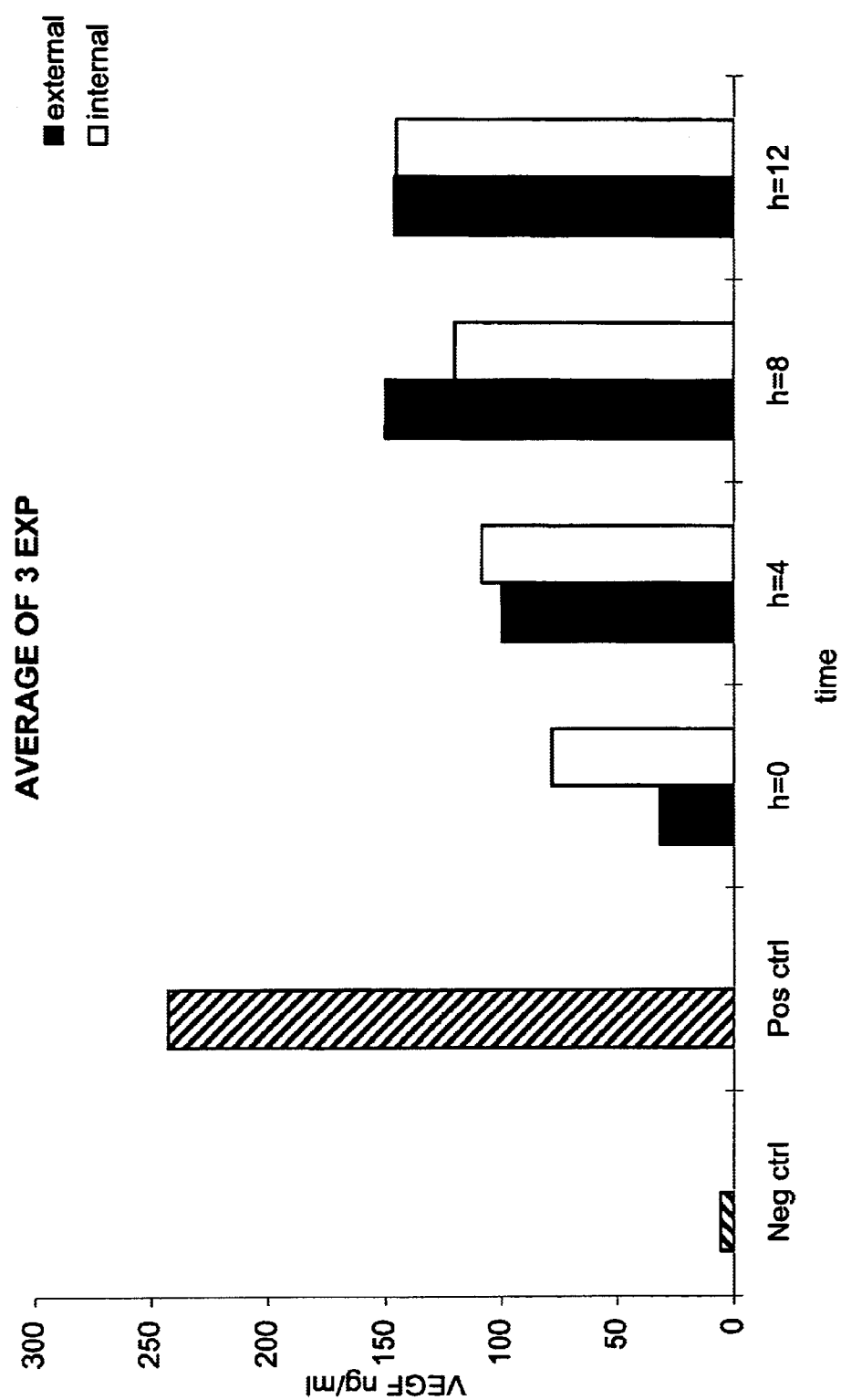
FIG. 2D is a bar graph showing the average release of VEGF under shear stress of 1.5 $dyn/cm^2$ according to FIGS. 2A–2C by a prosthetic graft of the present invention.

The results of three separate experiments are illustrated in FIGS. 2A–2C. FIG. 2D is a composite graph representing the average results of all three experiments. FIGS. 2A–2D demonstrate that a prosthetic vessel graft of the present invention produces significant and comparable amounts of VEGF protein both outside the graft and inside the graft under in vitro dynamic shear stress of 1.5 dyn/cm$^2$, with the amounts increasing over time.

Example 4

The following example demonstrates that a prosthetic graft of the present invention produces the recombinant protein both inside and outside of the graft under shear stress in vitro culture conditions.

Release of VEGF under dynamic condition-shear stress of 10 dyn/cm$^2$ during in vitro conditions was measured from the PhotoFix graft seeded perivascularly with rabbit aortic fibroblasts infected with AdV cmv VEGF as described in Example 1. Briefly, as described in Example 2 above, the seeded graft was mounted within a closed circuit placed in a chamber and connected to a peristaltic pump. As described in Example 3, 15 ml of medium were placed inside the PhotoFix and 300 ml of medium was placed in the incubation chamber outside the PhotoFix. The chamber was incubated in a humidified 5% $CO_2$ atmosphere at 37° C. under dynamic conditions of shear stress by circulating the medium through the circuit at a velocity of 10 dyn/cm$^2$ as indicated. The medium was collected and tested for VEGF as described in Example 2.

VEGF production was measured at given times (0, 4, 8, 12 hours) in the medium inside and outside the graft. For each time point, a different graft was used for the measurement. Negative and positive controls represent medium conditioned for 24 hours by uninfected fibroblasts or infected fibroblasts, respectively.

Figure 3A:
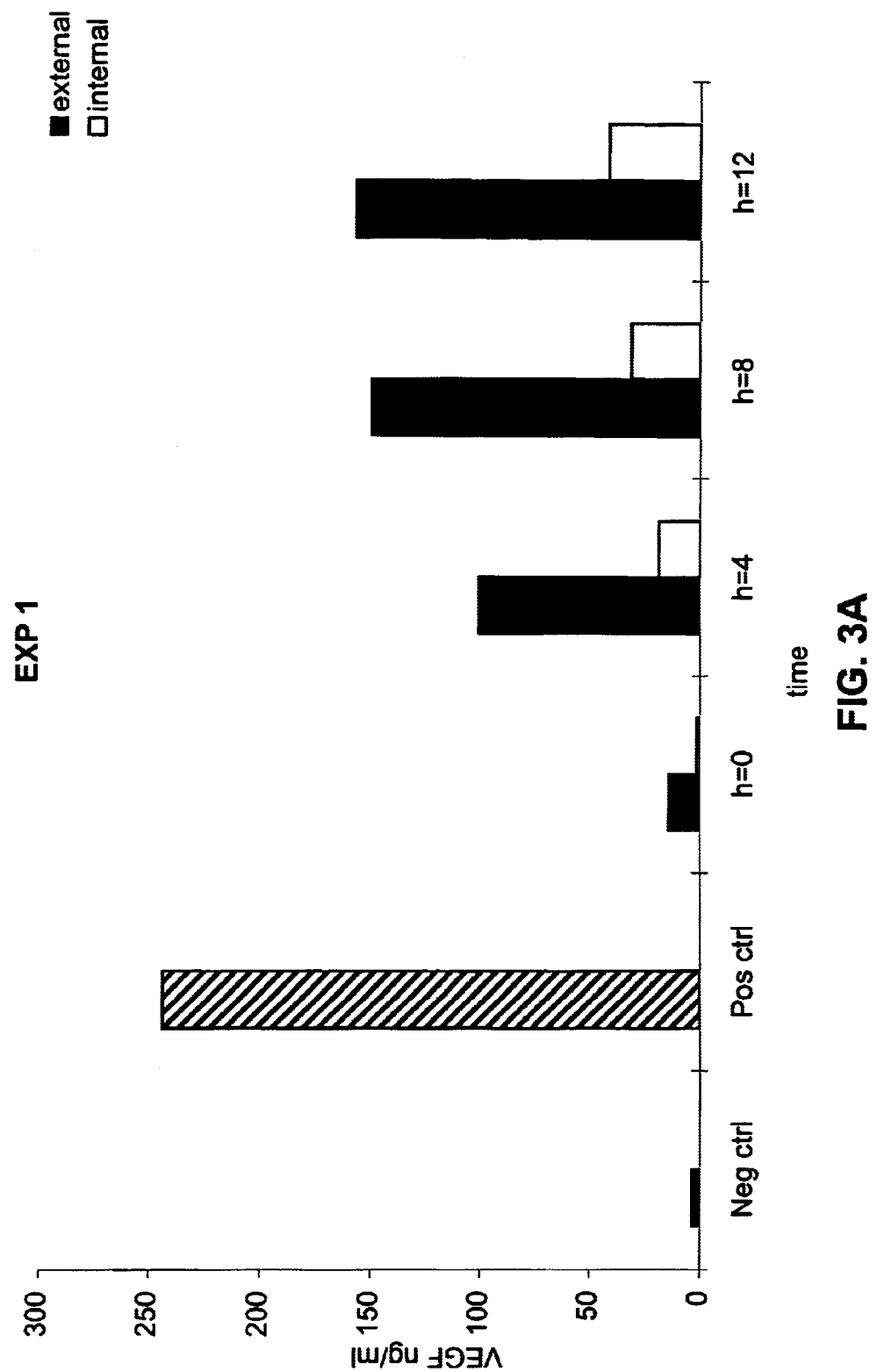
FIG. 3A is a bar graph showing the release of VEGF under shear stress of 10 $dyn/cm^2$ by a prosthetic graft of the present invention.
Figure 3B:
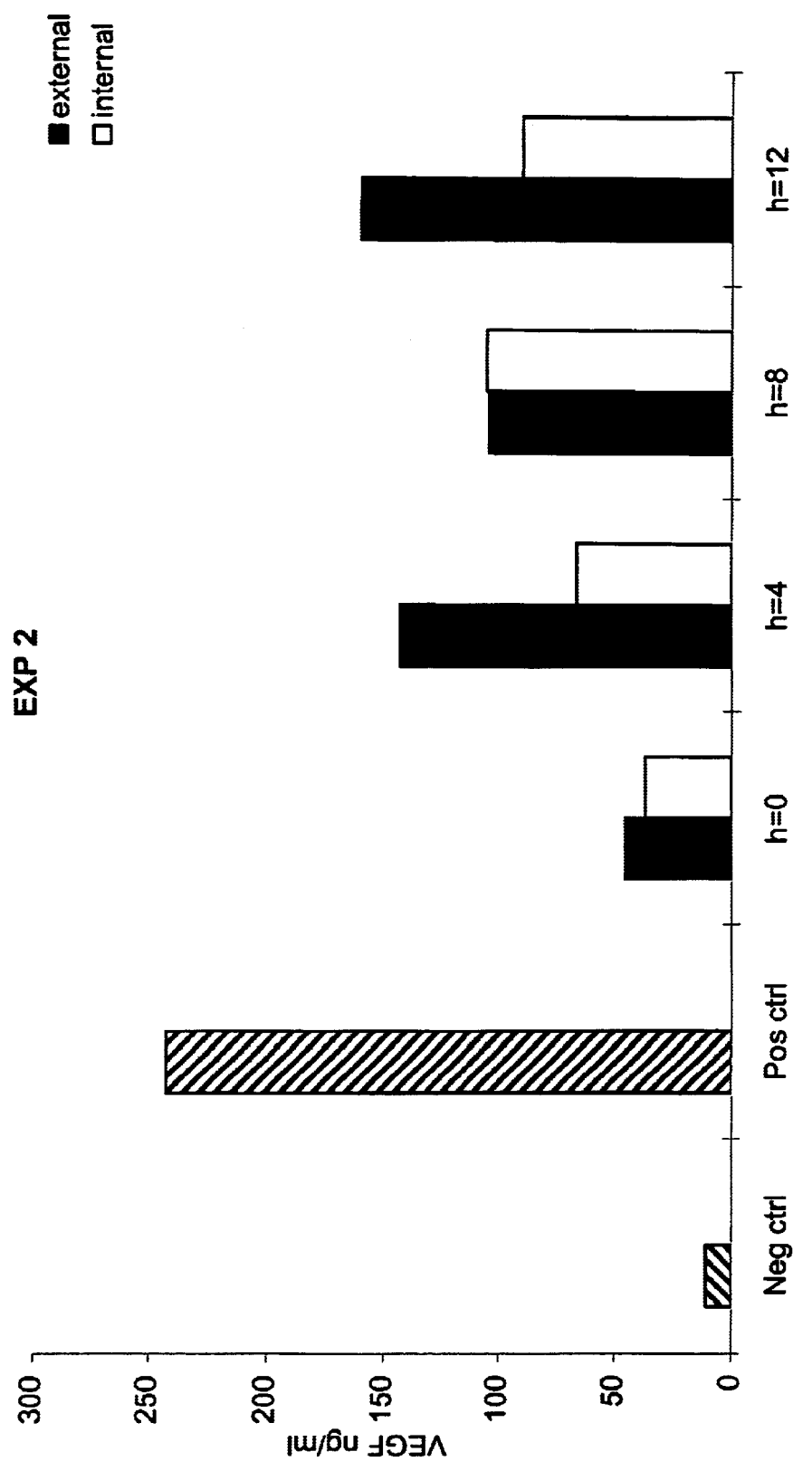
FIG. 3B is a bar graph showing the release of VEGF under shear stress of 10 $dyn/cm^2$ by a prosthetic graft of the present invention.
Figure 3C:
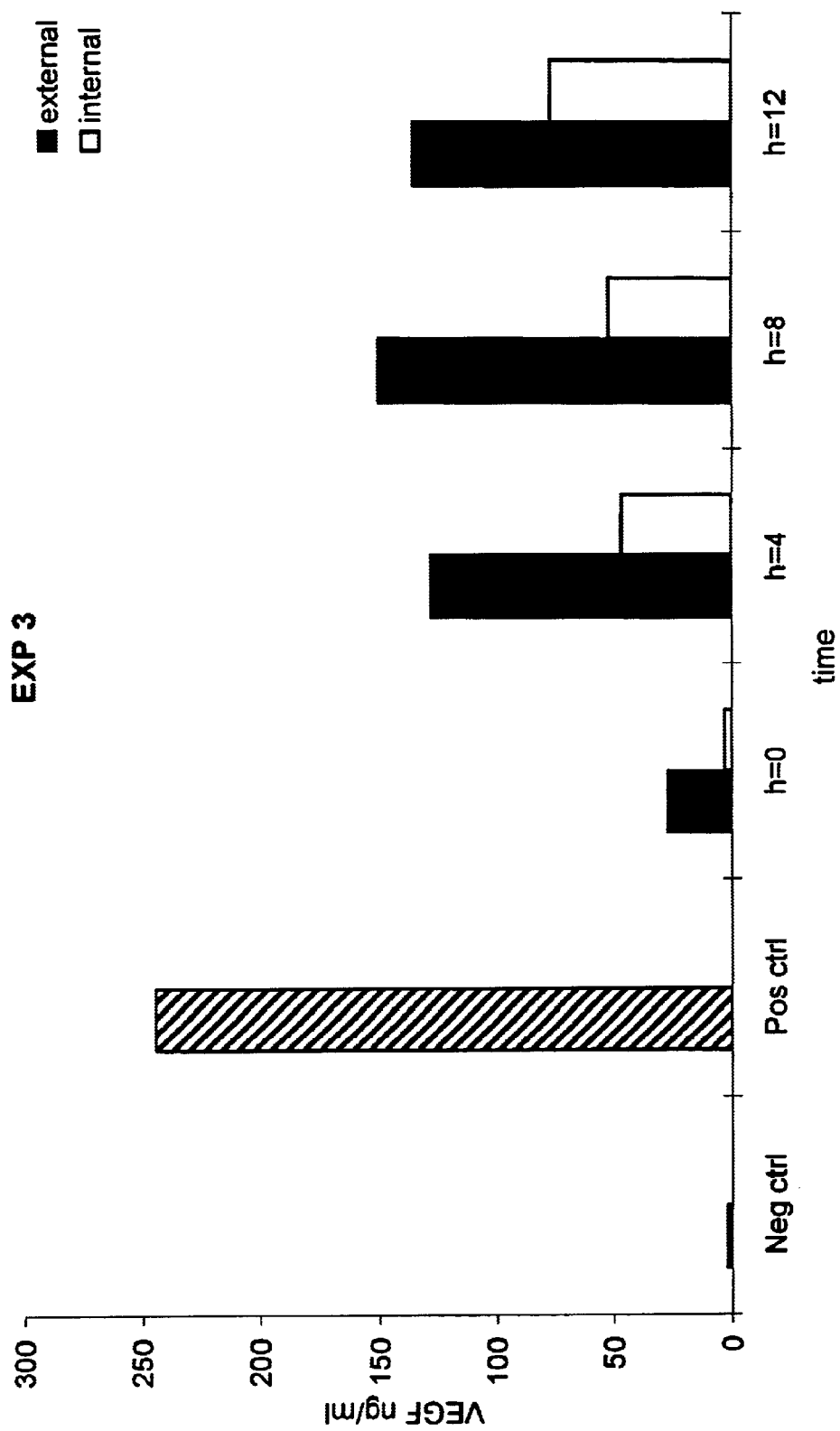
FIG. 3C is a bar graph showing the release of VEGF under shear stress of 10 $dyn/cm^2$ by a prosthetic graft of the present invention.
Figure 3D:
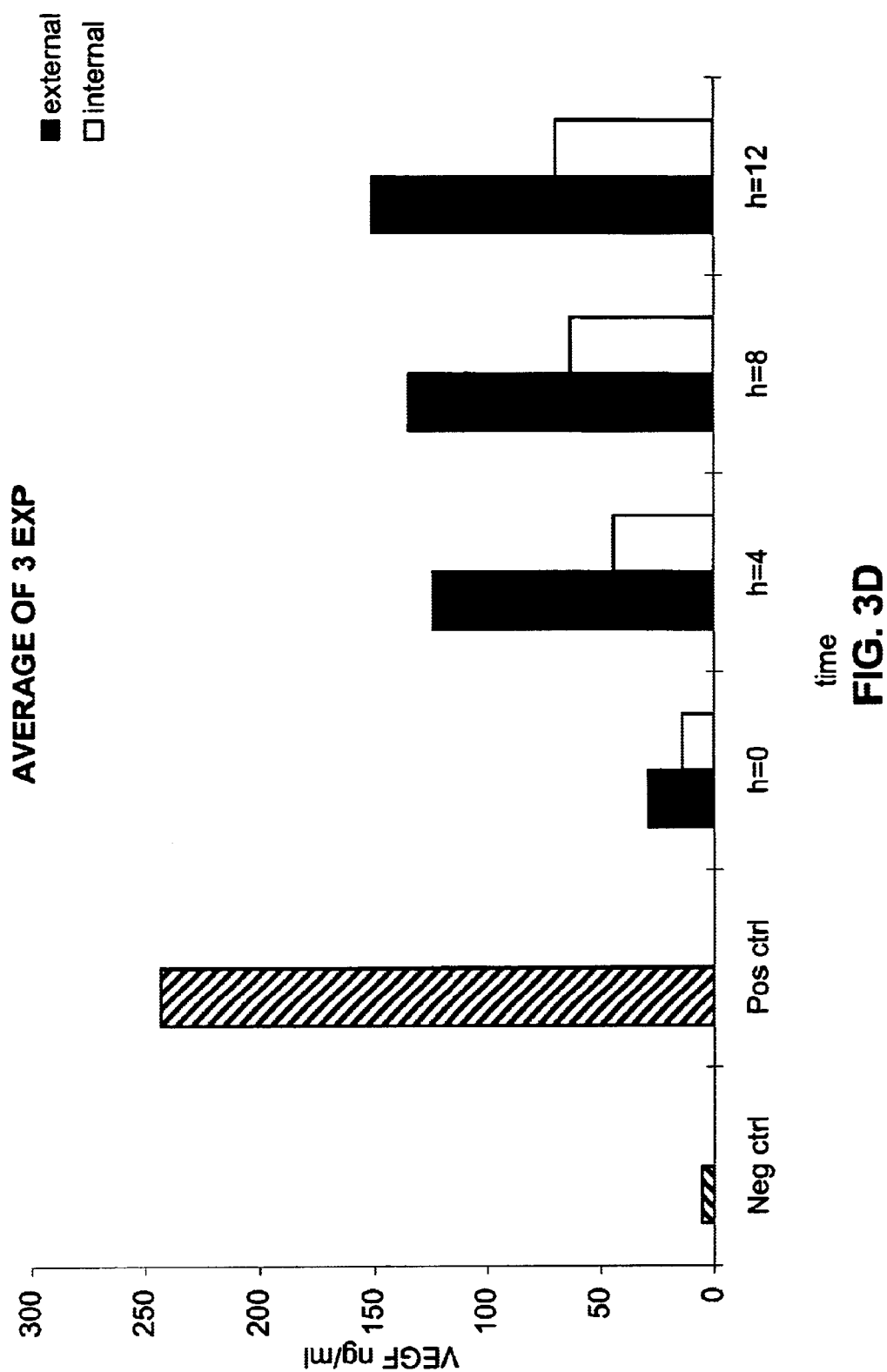
FIG. 3D is a bar graph showing the average release of VEGF under shear stress of 10 $dyn/cm^2$ according to FIGS. 3A–3C by a prosthetic graft of the present invention.

The results of three separate experiments are illustrated in FIGS. 3A–3C. FIG. 3D is a composite graph representing the average results of all three experiments. FIGS. 3A–3D demonstrate that, even under in vitro dynamic shear stress conditions of 10 dyn/cm$^2$, a prosthetic vessel graft of the present invention produces significant amounts of VEGF protein both outside the graft and inside the graft, with the amounts increasing over time.

Example 5

The following example demonstrates that a prosthetic graft of the present invention produces the recombinant protein in vivo.

In this study, fibroblasts were harvested from pig rectus muscle fascia and cultured for 3 weeks as described in Example 1. The fibroblasts were then transfected with the AdV cmv VEGF recombinant molecule, also as described in Example 1, and the recombinant fibroblasts were seeded onto PhotoFix grafts, also as described in Example 1. The grafts were incubated overnight in DMEM medium in 5% $CO_2$ at 37° C., and the seeded graft was implanted in carotid position in the same pig from which the fibroblast cells were isolated. Briefly, after sedation with retanine, a 30 kg domestic pig is anesthetized with halothane and mechanically ventilated. The neck is aseptically prepared and under sterile conditions, a longitudinal cervical incision is made to expose the common carotid artery of one side. The common carotid artery is isolated with vessel loops, and heparin (100U/kg) is given into the ear vein. The common carotid artery is then clamped proximally and distally leaving about 7 cm between the two clamps. A longitudinal arteriotomy is done distally to the proximal clamp, and the proximal end of a 5 cm long PhotoFix graft is anastomosed to the arteriotomy with a continuous suture of Prolene 6/0. A second arteriotomy is done proximally to the distal clamp (towards the brain) and the other extremity of the PhotoFix graft is sutured to the distal carotid as described before. Both anastomoses are therefore done using the end to side technique. The clamps are removed and hemostasis controlled with additional sutures, if required. The segment of common carotid artery that has been bypassed is then ligated proximally and distally and then removed. All blood then flows through the graft. Blood specimens are taken from the carotid before the bypass (control) and then from the internal jugular vein on the same side of the bypass, as blood passing into the graft and going to the brain returns to the heart by way of the same side internal jugular vein. Blood specimens are taken at fixed time points. To follow the production of the protein of interest produced by the seeded PhotoFix graft over long periods of time, a small polyethylene catheter is left inside the internal jugular vein and brought out to the skin by way of a subcutaneous tunnel. At the end of the procedure, the surgical planes are reapproximated and the animal is awakened and extubated before returning the animal to its cage.

In this experiment, blood samples were taken from the ipsilateral internal jugular vein before implant and then at 15 minutes, 30 minutes, 45 minutes, 1 hour, 12 hours, 24 hours and 96 hours after implant. VEGF levels were measured by ELISA as described in Example 2. FIG. 4 demonstrates that detectable levels of VEGF were seen as soon as 45 minutes after bypass (n.d.=non-detectable), and that such levels persisted until the end of the study (96 hours).

Example 6

The following example demonstrates that a prosthetic graft of the present invention produces the recombinant protein in vivo.

The experiment performed in Example 5 is repeated as described, but with the following modifications.
1. The production of the protein VEGF is controlled and measured over a longer period of time, (1 week, 2 weeks, 4 weeks and 8 weeks).
2. A control graft, not seeded with fibroblasts, is implanted on the opposite side of the seeded graft in the same animal in one additional animal group, and in another additional animal group, a control graft (not seeded) is implanted in the absence of a seeded graft on the opposite side.
3. The graft is seeded with cell types selected from the group of mesenchymal stem cells, bone marrow stem cells, embryonal stem cells, adipocytes, keratinocytes, vascular smooth muscle cells, platelets, or cells which have been genetically engineered to be adherent (e.g., genetically modified endothelial cells).
4. The graft is seeded with cells transfected with a protein selected from the group of vascular endothelial growth factor (VEGF), platelet-induced growth factor (PIGF), transforming growth factor β1 (TGFβ1), acidic fibroblast growth factor (aFGF), basic fibroblast growth factor (bFGF), transforming growth factor α (TGFα), epidermal growth factor, osteonectin, angiopoietin 1 (Ang1), Ang2, insulin-like growth factor (IGF), platelet-derived growth factor AA (PDGF-AA), PDGF-AB, PDGF-BB, tissue plasminogen activator (TPA), streptokinase, hirudin V, αv-βIII, urokinase plasminogen activator (uPA), nitric oxide synthase (NO synthase), or prostacyclin.
5. The graft is seeded with cells transfected alternate vectors which express the protein of interest.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed:
1. A prosthetic graft for containment of blood flow in vivo, comprising:
   (a) a porous prosthetic implant for containing blood in vivo, said prosthetic implant having an outer surface that is not in contact with blood flow in vivo and an inner surface that is in contact with blood flow in vivo, said inner surface defining an interior space for containment of blood flow; and,
   (b) naturally adherent cells adhered to the outer surface of said porous prosthetic implant, wherein said naturally adherent cells are not seeded on the inner surface of said porous prosthetic implant, wherein said naturally adherent cells are transfected with at least one recombinant nucleic acid molecule operatively linked to a transcription control sequence, said recombinant nucleic add molecule encoding a protein, wherein said protein is expressed by said cells ex vivo, wherein at least a portion of said protein, upon secretion from said cells, perfuses through pores of said prosthetic implant to said inner surface of said prosthetic implant, and wherein said protein is selected from the group consisting of a protein that enhances angiogenesis, a protein that inhibits thrombosis, a protein that causes thrombolysis, a protein that inhibits smooth muscle migration or proliferation and a vasodilator protein.
2. The prosthetic graft of claim 1, wherein said prosthetic implant is selected from the group consisting of, a prosthetic vessel, an artificial heart, a left ventricle assist device, and a dialysis shunt.
3. The prosthetic graft of claim 1, wherein said cells selected from the group consisting of fibroblasts, mesenchyinal stem cells, bone marrow stem cells, adipocytes, keratinocytes, vascular smooth muscle cells, and platelets.
4. The prosthetic graft of claim 1, wherein said naturally adherent cells are fibroblasts.
5. The prosthetic graft of claim 1, wherein said vasodilator protein is prostacyclin.
6. The prosthetic graft of claim 1, wherein said protein is selected from the group consisting of vascular endothelial growth factor (VEGF), platelet-induced growth factor (PIGF), transforming growth factor β1 (TGFβ1), acidic fibroblast growth factor (aFGF), basic fibroblast growth factor (bFGF), transforming growth factor α (TGFα), epidermal growth factor, osteonectin, angiopoietin 1 (Ang1), Ang2, insulin-like growth factor (IGF), platelet-derived growth factor AA (PDGF-AA), PDGF-AB and PDGF-BB.
7. The prosthetic graft of claim 1, wherein said protein is selected from the group consisting of tissue plasminogen activator (TPA), streptokinase, hirudin V, αv-β111, and urokinase plasminogen activator (uPA).
8. The prosthetic graft of claim 1, wherein said protein is nitric oxide synthase (NO synthase).
9. The prosthetic graft of claim 1, wherein said prosthetic implant is constructed of a material selected front the group consisting of highly resilient polyester, expanded polytetrafluorethylene (ePTFE), high porosity ePTFE, non-immunogenic xenogeneic tissue, porous silicon rubber, porous polyurethane, porous degradable polymer, and porous copolymers.
10. The prosthetic graft of claim 1, wherein the inner diameter of said prosthetic vessel is less than about 6 mm.
11. The prosthetic graft of claim 1, wherein said prosthetic implant is a large bore prosthetic vessel.
12. The prosthetic graft of claim 1, wherein said prosthetic implant has a pore size of from about 0.1 μm to about 500 μm.
13. A prosthetic graft for containment of blood flaw in vivo, comprising:
   (a) a porous prosthetic implant for containing blood in vivo, said prosthetic implant having an outer surface that is not in contact with blood flow in vivo and an inner surface that is in contact with blood flow in viva, said inner surface defining an interior space for containment of blood flow; and,
   (b) naturally adherent cells adhered to the outer surface of said porous prosthetic implant, wherein said naturally adherent cells are not seeded on the inner surface of said porous prosthetic implant, wherein said naturally adherent cells express and secrete at least one protein, wherein said protein is expressed by said cells ex vivo, and wherein at least a portion of said protein, upon secretion from said cells, perfuses through pores of said prosthetic implant to said inner surface of said prosthetic implant; and wherein said protein is selected from the group consisting of a protein that enhances angiogenesis, a protein that inhibits thrombosis, a protein that causes thrombolysis, a protein that inhibits smooth muscle migration or proliferation, and a vasodilator protein.
14. A method of implantation of a prosthetic graft for containment of blood flow, comprising implanting a prosthetic graft into a patient, said prosthetic graft comprising:
   (a) a porous prosthetic implant for containing blood in vivo, said prosthetic implant having an outer surface and an inner surface defining art interior space for containment of blood flow; and,
   (b) naturally adherent cells adhered to the outer surface of said porous prosthetic implant, wherein said naturally adherent cells are not seeded on the inner surface of said porous prosthetic implant, wherein said naturally adherent cells are transfected with at least one recombinant nucleic acid molecule operatively linked to a transcription control sequence, said recombinant nucleic acid molecule encoding a protein, wherein at least a portion of said protein, upon secretion from said cells, perfuses through pores of said prosthetic implant to said inner surface of said prosthetic implant and wherein said protein is selected from the group consisting of a protein that enhances a protein that inhibits thrombosis, a protein that causes thrombolysis, a protein that inhibits smooth muscle migration or proliferation, and a vasodilator protein;

and wherein, prior to implantation of said graft into a patient, said cells express said protein in vitro.

15. The method of claim 14, wherein said cells are autologous to said patient.

16. The method of claim 14, wherein said prosthetic graft is used as an arterial or venous replacement.

17. A method for implantation of a prosthetic graft for containing blood how in a patient, comprising:

(a) harvesting fibroblast veils from a patient in need of a prosthetic graft for containing blood flow;

(b) transfecting said fibroblast cells with an isolated nucleic acid molecule encoding a protein selected from the group consisting of a protein that enhances angiogenesis, a protein that inhibits thrombosis, a protein that causes thrombolysis, a protein that inhibits smooth muscle migration or proliferation, and a vasodilator protein;

(c) applying said transfected fibroblast cells onto a prosthetic implant configured for containing blood flow in vivo, wherein said prosthetic implant has an outer surface that is not in contact with blood flow in vivo and an inner surface that is in contact with blood flow in vivo, said inner surface defining an interior surface for containment of blood flow, wherein said transfected fibroblast cells are applied to said outer surface and not to said inner surface for a time sufficient to allow said fibroblast cells to adhere to said outer surface to form a prosthetic graft;

wherein, prior to implantation of said implant into a patient, said fibroblast cells express said protein in vitro, and wherein at least a portion of said protein, upon secretion from said cells, perfuses through pores of said prosthetic graft to a surface in contact with blood flow; and (d) implanting said prosthetic graft into sand patient.

18. A method of providing endothelial cell growth factors to a vascular graft, comprising applying naturally adherent cells to a porous prosthetic vessel having a perivascular surface and a lumenal surface, wherein said naturally adherent cells are adhered to the perivascular surface of the prosthetic vessel and are not applied to the lumenal surface of the graft; and wherein said naturally adherent cells are transfected with at least one recombinant nucleic acid molecule operatively linked to a transcription control sequence, said recombinant nucleic acid molecule encoding a an endothelial cell growth factor;

whereby said protein is expressed and secreted by said adherent cells ex vivo, and wherein at least a portion of said protein perfuses through pores in said prosthetic vessel to the luminal surface of said prosthetic vessel.

* * * * *